US006974798B2

(12) United States Patent
Gao

(10) Patent No.: US 6,974,798 B2
(45) Date of Patent: Dec. 13, 2005

(54) TREATMENT OF BALANCE IMPAIRMENTS

(75) Inventor: Wei-Qiang Gao, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 306 days.

(21) Appl. No.: 10/096,762

(22) Filed: Mar. 12, 2002

(65) Prior Publication Data

US 2002/0169124 A1 Nov. 14, 2002

Related U.S. Application Data

(63) Continuation of application No. 09/664,295, filed on Sep. 18, 2000, now Pat. No. 6,429,196, which is a continuation of application No. 08/581,662, filed on Dec. 29, 1995, now Pat. No. 6,121,235.

(51) Int. Cl.[7] .................. A61K 31/70; A61K 33/24; A61K 38/00; G01N 33/00; G01N 33/48
(52) U.S. Cl. ..................... 514/12; 514/21; 514/29; 514/34; 514/37; 514/41; 424/649; 436/63; 436/86; 436/87
(58) Field of Search .................. 514/12, 21, 29, 514/34, 37, 41; 436/63, 86, 87; 424/649

(56) References Cited

U.S. PATENT DOCUMENTS

| 6,121,235 A | * | 9/2000 | Gao | .............................. | 514/12 |
| 6,429,196 B1 | * | 8/2002 | Gao | .............................. | 514/12 |

OTHER PUBLICATIONS

Anniko et al., "Cisplatin: Evaluation of its Ototoxic Potential" *Am. J. Otolaryngol.* 7:276–293 (1986).
Apfel et al., "Nerve Growth Factor Prevents Toxic Neuropathy in Mice" *Annals of Neurology* 29(1):87–90, (Jan. 1991).
Ard et al., "Trophic Interactions Between the Cochleovestibular Ganglion of the Chick Embryo and its Synaptic Targets in Culture" *Neuroscience* 16(1):151–170 (1985).
Au et al., "Aminoglycoside Antibiotics Preferentially Increase Permeability in Phosphoinositide–containing membranes: a Study with Carboxyfluorescein in Liposomes" *Biochimica et Biophysica Acta* 902:80–86 (1987).
Baird et al., "Cerebellar Target Neurons Provide a Stop Signal for Afferent Neurite Extension in vitro" *The Journal of Neuroscience* 12(2):619–634 (Feb. 1992).
Barbacid, "The Trk Family of Neurotrophin Receptors: Molecular Characterization and Oncogenic Activation in Human Tumors" *Molecular Genetics of Nervous System Tumors* pps. 123–136 (1993).
Barde et al., "Purification of a New Neurotrophic Factor From Mammalian Brain" *EMBO Journal* 1(5):549–553 (1982).
Bareggi et al., "Gentamicin Ototoxicity: Histological and Ultrastructural Alterations After Transtympanic Administration" *Pharmacological Research* 22(5):635–644 (1990).

Barker et al., "Disruption of NGF Binding to the Low Affinity Neurotrophin Receptor $p75^{LNTR}$ Reduces NGF Binding to TrkA on PC12 Cells" *Neuron* 13:203–215 (1994).
Berggren et al., "Intermediate Filament Proteins in the Embryonic Inner Ear of Mice Under Normal Conditions and After Exposure to Ototoxic Drugs" *Acta Otolaryngol* 109:57–65 (1990).
Berkemeier et al., "Neurotrophin–5: A Novel Neurotrophic Factor That Activates trk and trkB" *Neuron* 7:857–866 (Nov. 1991).
Boettcher et al., "Concentration of Salicylate in Serum and Perilymph of the Chinchilla" *Arch. Otoloaryngol Head Neck Surg.* 116:681–684 (1990).
Boettcher et al., "Effects of Sodium Salicylate on Evoked–response Measures of Hearing" *Hearing Research* 42:129–142 (1989).
Boettcher et al., "Salicylate Ototoxicity: Review and Synthesis" *Am. J. Otoloaryngol.* 12:33–47 (1991).
Carenza et al., "Peripheral Neuropathy and Ototoxicity of Diclorodiamineplatinum: Instrumental Evaluation" *Gynecologic Oncology* 25:244–249 (1986).
Chao, "Gene Transfer and Molecular Cloning of the Human NGF Receptor" *Science* 232:518–521 (1986).
Chao, "Growth Factor Signaling: Where is the Specificity?" *Cell* 68:995–997 (Mar. 20, 1992).
Clary et al., "An Alternatively Spliced Form of the Nerve Growth Factor Receptor TrkA Confers an Enhanced Response to Neurotrophin 3" *Proc. Natl. Acad. Sci. USA* 91:11133–11137 (1994).
Clary et al., "TrkA Cross–linking Mimics Neuronal Responses to Nerve Growth Factor" *Molecular Biology of the Cell* 5:549–563 (1994).
Cohen et al., "Neurotrophin–4/5 (NT–4/5) Increases Adult Rat Retinal Ganglion Cell Survival and Neurite Outgrowth in vitro" *Journal of Neurobiology* 25(8):953–959 (1994).
Cordon–Cardo et al., "The trk Tyrosine Protein Kinase Mediates the Mitogenic Properties of Nerve Growth Factor and Neurotrophin–3" *Cell* 66:173–183 (Jul. 12, 1991).
Corwin et al., "Auditory Hair Cells: Structure, Function, Development, and Regeneration" *Annu. Rev. Neuroscience* 14:301–333 (1991).
Cotanche et al., "Regeneration of Hair Cells in the Vestibulocochlear System of Birds and Mammals" *Current Opinion in Neurobiology* 4:509–514 (1994).

(Continued)

*Primary Examiner*—Raymond J. Henley, III
*Assistant Examiner*—Leslie A. Royds
(74) *Attorney, Agent, or Firm*—Ginger R. Dreger; Atulya R. Agarwal; James A. Fox

(57) ABSTRACT

Compositions and methods are provided for prophylactic or therapeutic treatment of balance impairments involving neuronal damage, loss, or degeneration, preferably of vestibular ganglion neurons, in an animal by administration of an effective amount of a trkB or trkC agonist, particularly a neurotrophin, more preferably NT–4/5.

19 Claims, 5 Drawing Sheets

OTHER PUBLICATIONS

Davies et al., "Different Factors From the Central Nervous System and Periphery Regulate the Survival of Sensory Neurones" *Nature* 319:497–499 (1986).

Davies et al., "Neurotrophin–4/5 Is a Mammalian–specific Survival Factor for Distinct Populations of Sensory Neurons" *J. Neuroscience* 13(11):4961–4967 (Nov. 1993).

Davies et al., "p75–Deficient Trigeminal Sensory Neurons Have an Altered Response to NGF but Not to Other Neurotrophins" *Neuron* 11:565–574 (Oct. 1993).

De Moura, "Inner Ear Pathology in Acoustic Neurinoma" *Arch. Otolaryng.* 85:21–29 (125–133) (Feb. 1967).

Dublin, "Anatomic Principles With Some Functional and General Pathologic Applications" *Fundamentals of Sensorineural Auditory Pathology* (Chapter 3), Springfield, Illinois: Charles C. Thomas pps. 18–103 (1976).

Duckert et al., "Morphological Correlates of Functional Recovery in the Chicken Inner Ear After Gentamycin Treatment" *The Journal of Comparitive Neurology* 331:75–96 (1993).

Ernfors et al., "Function of the Neurotrophins in the Auditory and Vestibular Systems: Analysis of BDNF and NT–3 Gene Knockout Mice" *ARO Abstracts* (abstract 759) pps. 190 (1995).

Ernfors et al., "Mice Lacking Brain–derived Neurotrophic Factor Develop with Sensory Deficits" *Nature* 368:147–149 (Mar. 10, 1994).

Ernfors et al., "Molecular Cloning and Neurotrophic Activities of a Protein With Structural Similarities to Nerve Growth Factor: Developmental and Topographical expression in the brain" *Proc. Natl. Acad. Sci. USA* 87:5454–5458 (Jul. 1990).

Escandon et al., "Regulation of Neurotrophin Receptor Expression During Embryonic and Postnatal Development" *The Journal of Neuroscience* 14(4):2054–2068 (Apr. 1994).

Falbe–Hansen, "Clinical and Experimental Histological Studies on Effects of Salicylate and Quinine on the Ear" *Acta Otolaryng. Supp.* 44:1–216 (1941).

Farinas et al., "Severe Sensory and Sympathetic Deficits in Mice Lacking Neurotrophin–3" *Nature* 369:658–661 (Jun. 23, 1994).

Fischer et al., "Reversal of Spatial Memory Impairments in Aged Rats by Nerve Growth Factor and Neurotrophins 3 and 4/5 but not by Brain–Derived Neurotrophic Factor" *Proc. Natl. Acad. Sci. USA* 91:8607–8611 (Aug. 1994).

Forge et al., "Ultrastructural Evidence for Hair Cell Regeneration in the Mammalian Inner Ear" *Science* 259:1616–1619 (Mar. 12, 1993).

Fritzsch, "Mice Homozygous for a Non–functional trk–B Receptor Lack Selectively in th Innervation of Semicircular Canals" *ARO Abstracts* (Abstract 760) pps. 190 (1995).

Furley et al., "The Axonal Glycoprotein TAG–1 is an Immunoglobulin Superfamily Member with Neurite Outgrowth–Promoting Activity" *Cell* 61:157–170 (Apr. 6, 1990).

Gao et al., "Cerebellar Granule Cell Neurogenesis is Regulated by Cell–Cell Interactions in Vitro" *Neuron* 6:705–715 (May 1991).

Gao et al., "Neurotrophin–3 Reverses Experimental Cisplatin–induced Peripheral Sensory Neuropathy" *Annals of Neurology* 38(1):30–37 (Jul. 1995).

Gao et al., "Neurotrophin–4/5 (NT–4/5) and Brain–Derived Neurotrophic Factor (BDNF) Act at Later Stages of Cerebellar Granule Cell Differentiation" *The Journal of Neuroscience* 15(4):2656–2667 (Apr. 1995).

Garner et al., "Isoforms of the Avian TrkC Receptor: A Novel Kinase Insertion Dissociates Transformation and Process Outgrowth From Survival" *Neuron* 13:457–472 (1994).

Gotz et al., "Neurotrophin–6 is a New Member of the Nerve Growth Factor Family" *Nature* 372:266–269 (1994).

Gotz et al., "Production and Characterization of Recombinant Mouse Neurotrophin–3" *European Journal of Biochemistry* 204:745–749 (1992).

Guild et al., "Correlations of Differences in the Density of Innervation of the Organ of Corti with Differences in the Acuity of Hearing. Including Evidence as to the Location in the Human Cochlea of the Receptors for Certain Tones" *Acta Oto–Laryngologica.* Holmgren vol. XV:269–308 (1931).

Jones et al., "Molecular Cloning of a Human Gene That is a Member of the Nerve Growth Factor Family" *Proc. Natl. Acad. Sci. USA* 87:8060–8064 (1990).

Kaplan et al., "The trk Proto–Oncogene Product: A Signal Transducing Receptor for Nerve Growth Factor" *Science* 252:554–558 (Apr. 26, 1991).

Kaplan et al., "Tyrosine Phosphorylation and Tyrosine Kinase Activity of the trk Proto–oncogene Product Induced by NGF" *Nature* 350:158–160 (Mar. 14, 1991).

Kelley et al., "The Development Organ of Corti Contains Retinoic Acid and Forms Supernumerary Hair Cells in Response to Exogenous Retinoic Acid in Culture" *Development* 119:1041–1053 (1993).

Klein et al., "Expression of the Tyrosine Kinase Receptor Gene trkB is Confined to the Murine Embryonic and Adult Nervous System" *Development* 109:845–850 (1990).

Klein et al., "The trk Proto–Oncogene Encodes a Receptor for Nerve Growth Factor" *Cell* 65:189–197 (Apr. 5, 1991).

Klein et al., "The trk Tyrosine Protein Kinase Is a Receptor for Brain–Derived Neurotrophic Factor and Neurotrophin–3" *Cell* 66:395–403 (Jul. 26, 1991).

Klein et al., "The trkB Tyrosine Protein Kinase Is a Receptor for Neurotrophin–4" *Neuron* 8:947–956 (May 1992).

Klein et al., "trkB, A Novel Tyrosine Protein Kinase Receptor Expressed During Mouse Neural Development" *EMBO Journal* 8(12):3701–3709 (1989).

Knusel et al., "Brain–derived Neurotrophic Factor Administration Protects Basal Forebrain Cholinergic but Not Nigral Dopaminergic Neurons from Degenerative Changes after Axotomy in the Adult Rat Brain" *The Journal of Neuroscience* 12(11):4391–4402 (Nov. 1992).

Koliatsos et al., "Evidence That Brain–Derived Neurotrophic Factor is a Trophic Factor for Motor Neurons in vivo" *Neuron* 10:359–367 (Mar. 1993).

Konings et al., "Reversal by NGF of Cytostatic Drug–induced Reduction of Neurite Outgrowth in Rat Dorsal Root Ganglia in vitro" *Brain Research* 640:195–204 (1994).

Kopf–Maier et al., "Changes in the Cytoskeleton Pattern of Tumor Cells by Cisplatin in vitro" *Chem–Biol. Interactions* 82:295–316 (1992).

Korsching, "The Neurotrophic Factor Concept: A Reexamination" *The Journal of Neuroscience* 13(7):2739–2748 (1993).

Lamballe et al., "trkC, a New Member of the trk Family of Tyrosine Protein Kinases, Is a Receptor for Neurotrophin–3" *Cell* 66:967–979 (Sep. 6, 1991).

Lambert, "Inner Ear Hair Cell Regeneration in a Mammal: Identification of a Triggering Factor" *Laryngoscope* 104:701–718 (1994).

Larkfors et al., "Effects of Neurotrophins on Rat Embryonic Cerebellar Purkinje Cells in Vitro" *Society for Neuroscience Abstracts* (Abstract 278.14) 19:667 (1993).

Leake et al., "Chronic Intracochlear Electrical Stimulation in Neonatally Deafened Cats: Effects of Intensity and Stimulating Electrode Location" *Hearing Research* 64:99–117 (1992).

Lefebvre et al., "Neurotrophins Affect Survival and Neuritogenesis by Adult Injured Auditory Neurons in vitro" *NeuroReport* 5(8):865–868 (1994).

Lefebvre et al., "Retinoic Acid Stimulates Regeneration of Mammalian Auditory Hair Cells" *Science* 260:692–695 (Apr. 30, 1993).

Lefebvre et al., "Temporal Pattern of Nerve Growth Factor (NGF) Binding in vivo and the in vitro Effects of NGF on Cultures of Developing Auditory and Vestibular Neurons" *Acta Otolaryngol* 111:304–311 (1991).

Leibrock et al., "Molecular Cloning and Expression of Brain–derived Neurotrophic Factor" *Nature* 341:149–152 (Sep. 14, 1989).

Levi–Montalcini, "The Nerve Growth Factor: Thirty–five Years Late" *The EMBO Journal* 6(5):1145–1154 (1987).

Lim, "Effects of Noise and Ototoxic Drugs at the Cellular Level in the Cochlea: A Review" *Am. J. Otolaryngol* 7(2):73–99 (Mar. 1986).

Lippe et al., "Loss of Avian Spiral Ganglion Neurons Following Aminoglycoside–induced Hair Cell Loss and Regeneration" *Assoc. Res. Otoloaryngol. Abstracts* (Abstract 336) pps. 84 (1995).

Maisonpierre et al., "Neurotrophin–3: A Neurotrophic Factor Related to NGF and BDNF" *Science* 247:1446–1451 (Mar. 23, 1990).

Martin–Zanca et al., "Molecular and Biochemical Characterization of the Human trk Proto–Oncogene" *Molecular & Cellular Biology* 9(1):24–33 (Jan. 1989).

McAlpine et al., "The Ototoxic Mechanism of Cisplatin" *Hearing Research* 47:191–204 (1990).

McCabe et al., "The Effect of Aspirin Upon Auditory Sensitivity" *The Annals of Otology Rhinology & Laryngology* LXXXI(2):312–325 (1965).

Mollman, "Cisplating Neurotoxicity" *New England J. of Medicine* 322(2):126–127 (Jan. 11, 1990).

Myers et al., "Salicylate Ototoxicity" *Arch Otolaryng* 82:483–493 (1965).

Nakai et al., "Ototoxicity of the Anticancer Drug Cisplatin" *Acta Otoloaryngol* 93:227–232 (1982).

Pirvola et al., "Brain–derived Neurotrophic Factor and Neurotrophin 3 mRNAs in the Peripheral Target Fields of Developing Inner Ear Ganglia" *Proc. Natl. Acad. Sci. USA* 89:9915–9919 (1992).

Pryor, "Assessment of Auditory Dysfunction" *Principles of Neurotoxicology*, Louis W. Chang, New York:Marcel Dekker, Inc. pps. 345–371 (1994).

Rastel et al., "An Original Organotypic Culture Method to Study the Organ of Corti of the Newborn Rat in vitro" *Journal of Neuroscience Methods* 47:123–131 (1993).

Richardson et al., "Cochlear Cultures as a Model System for Studying Aminoglycoside Induced Ototoxicity" *Hearing Research* 53:293–311 (1991).

Roelofs et al., "Peripheral Sensory Neuropathy and Cisplatin Chemotherapy" *Neurology* 34:934–938 (Jul. 1984).

Rosenthal et al., "Primary Structure and Biological Activity of a Novel Human Neurotrophic Factor" *Neuron* 4:767–773 (May 1990).

Rybak, "Ototoxic Mechanisms" *Neurobiology of Hearing: The Chochlea*, R.A. Altschuler, New York: Raven Press pps. 441–454 (1986).

Schacht, "Molecular Mechanisms of Drug–induced Hearing Loss" *Hearing Research* 22:297–304 (1986).

Schecterson et al., "Neurotrophin and Neurotrophin Receptor mRNA Expression in Developing Inner Ear" *Hearing Research* 73:92–100 (1994).

Scopes, "Protein Purification: Principles and Practice" *Springer Advanced Texts in Chemistry*, Springer Advanced Texts in Chemistry pps. 176–181 (1987).

Sera et al., "Morphological Changes in the Vestibular Epithelia and Ganglion Induced by Ototoxic Drug" *Scanning Microscopy* 1(3):1191–1197 (1987).

Shelton et al., "Human trks: Molecular Cloning, Tissue Distribution, and Expression of Extracellular Domain Immunoadhesins" *The Journal of Neuroscience* 15(1):477–491 (1995).

Siegal et al., "Cisplatin–induced Peripheral Neuropathy" *Cancer* 66:1117–1123 (1990).

Snider, "Functions of the Neurotrophins During Nervous System Development: What the Knockouts Are Teaching Us" *Cell* 77:627–638 (Jun. 3, 1994).

Sobkowicz et al., "Organotypic Development of the Organ of Corti in Culture" *Journal of Neurocytology* 4:543–572 (1975).

Soppet et al., "The Neurotrophic Factors Brain–Derived Neurotrophic Factor and Neurotrophin–3 Are Ligands for the trkB Tyrosine Kinase Receptor" *Cell* 65:895–903 (May 31, 1991).

Squinto et al., "trkB Encodes a Functional Receptor for Brain–Derived Neurotrophic Factor and Neurotrophin–3 but Not Nerve Growth Factor" *Cell* 65:885–893 (May 31, 1991).

Stadnicki et al., "Cis–dichlorodiammineplatinum (II) (NSC–119875): Hearing Loss and Other Toxic Effects in Rhesus Monkeys" *Cancer Chemotherapy Reports* 59(3):467–480 (May/Jun. 1975).

Thompson et al., "Cisplatin Neuropathy" *Cancer* 54:1269–1275 (1984).

Tsoulais et al., "The Rat trkC Locus Encodes Multiple Neurogenic Receptors That Exhibit Differential Response to Neurotrophin–3 in PC12 Cells" *Neuron* 10:975–990 (May 1993).

Tsue et al., "Diffusible Factors Regulate Hair Cell Regeneration in the Avian Inner Ear" *Proc. Natl. Acad. Sci. USA* 91:1584–1588 (Feb. 1994).

Tsue et al., "Hair Cell Regeneration in the Inner Ear" *Otoloaryngol Head Neck Surg.* 111:281–301 (1994).

Valenzuela et al., "Alternative Forms of Rat TrkC with Different Functional Capabilities" *Neuron* 10:963–974 (May 1993).

Vazquez et al., "Pattern of trk B Protein–Like Immunoreactivity in vivo and in vitro Effects of Brain–derived Neurotrophic Factor (BDNF) on Developing Cochlear and Vestibular Neurons" *Anat. Embryol.* 189:157–167 (1994).

Verdi et al., "p75$^{LNGFR}$ Regulates Trk Signal Transduction and NGF–Induced Neuronal Differentiation in MAH Cells" *Neuron* 12:733–745 (Apr. 1994).

von Bartheld et al., "Expression of Nerve Growth Factor (NGF) Receptors in the Devleoping Inner Ear of Chick and Rat" *Development* 113:455–470 (1991).

Warchol et al., "Regenerative Proliferation in Inner Ear Sensory Epithelia From Adult Guinea Pigs and Humans" *Science* 259:1619–1622 (Mar. 12, 1993).

Weskamp et al., "Evidence That Biological Activity of NGF is Mediated Through a Novel Subclass of High Affinity Receptors" *Neuron* 6:649–663 (Apr. 1991).

Wheeler et al., "Expression of BDNF and NT–3 mRNA in Hair Cells of the Organ of Corti: Quantitative Analysis in Developing Rats" *Hearing Research* 73:46–56 (1994).

Windebank et al., "The Effect of Nerve Growth Factor, Ciliary Neurotrophic Factor, and ACTH Analogs on Cisplatin Neurotoxicity in vitro" *Neurology* 44:488–494 (Mar. 1994).

Wittmaack, "Beitrage zur Kenntnis der Wirkung des Chinins auf das Gehorargan" *Physiologie,* Pfluger, Funfundneunzigster Band pps. 237–263 (1903).

Woodford et al., "Effects of Combinations of Sodium Salicyalte and Noise on the Auditory Threshold" *Ann. Otol.* 87:117–127 (1987).

Yamashita et al., "Induction of Cell Proliferation in Mammalian Inner–ear Sensory Epithelia by Transforming Growth Factor α and Epidermal Growth Factor" *Proc. Natl. Acad. Sci. USA* 92:3152–3155 (1995).

Yan et al., "Brain–derived Neurotrophic Factor Rescues Spinal Motor Neurons From Axotomy–induced Cell Death" *Nature* 360:753–755 (1992).

Yan et al., "Distribution of Interacerebral Ventricularly Administered Neurotropins in Rat Brain and Its Correlation with Trk Receptor Expression" *Experimental Neurology* 127:23–36 (1994).

Ylikoski et al., "Expression Patterns of Neurotrophin and Their Receptor mRNA in the Rat Inner Ear" *Hearing Research* 65:69–78 (1993).

Zheng et al., "Neurotrophin–4/5 Enhances. Survival of Cultured Spiral Ganglion Neurons and Protects Them From Cisplatin Neurotoxicity" *The Journal of Neuroscience* 15(7):5079–5087 (1995).

Zheng et al., "Neurotrophin–4/5, Brain–Derived Neurotrophic Factor, and Neurotrophin–3 Promote Survival of Cultured Vestibular Ganglion Neurons and Protect Them Against Neurotoxicity of Ototoxins" *Journal of Neurobiology* 28(3):330–340 (1995).

\* cited by examiner

TREATMENT OF BALANCE IMPAIRMENTS

This application claims the benefit under 35 U.S.C. §120 as a continuation of U.S. patent application Ser. No. 09/664,295, filed Sep. 18, 2000, now U.S. Pat. No. 6,429, 196, which is a continuation of U.S. patent application Ser. No. 08/581,662, filed Dec. 29, 1995, now U.S. Pat. No. 6,121, 235.

BACKGROUND

1. Field of the Invention

This application relates to methods for prophylactic and therapeutic treatment of balance impairments. More particularly, the application relates to prevention or therapy of ototoxin-induced balance impairments by administration of neurotrophins.

Introduction

Balance impairments are serious handicaps which affect millions of people. Balance impairments can be attributed to a wide variety of causes, including infections, mechanical injury, loud sounds, aging, and chemical-induced ototoxicity that damage neurons and/or hair cells of the peripheral vestibular systems. Vestibular ganglion neurons ("VGN"), which are primary afferent sensory neurons responsible for balance, deliver signals from the utricle, saccule and ampullae of the inner ear to the brain through the eighth nerve connecting primary auditory neurons in the spiral ganglia to the brain stem. Damage to the peripheral auditory system is responsible for a majority of balance deficits (Dublin, 1976; Lim, 1986) with destruction of vestibular ganglia neurons as a major cause of balance impairments.

During embryogenesis, the vestibular ganglion, spiral ganglion, and the otic vesicle are derived from the same neurogenic ectoderm, the otic placode. The vestibular ganglion neurons send peripheral neuronal projections to hair cells of the inner ear and extend central projections to the brainstem nuclei. This system is sensitive to ototoxins that include therapeutic drugs, antineoplastic agents, contaminants in foods or medicines, and environmental and industrial pollutants. Ototoxic drugs include the widely used chemotherapeutic agent cisplatin and its analogs (Fleischman et al., 1975; Stadnicki et al., 1975; Nakai et al., 1982; Berggren et al., 1990), commonly used aminoglycoside antibiotics, e.g. gentamicin, for the treatment of infections caused by Gram-negative bacteria, (Sera et al., 1987; Hinojosa and Lerner, 1987; Bareggi et al., 1990), quinine and its analogs, salicylate and its analogs, and loop-diuretics.

The toxic effects of these drugs on vestibular ganglion neurons are often the limiting factor for their therapeutic usefulness. For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman and Gilman et al., eds; Macmillan Publishing Co., Inc., New York, pp. 1169–71 (1980)). Aminoglycoside antibiotics are generally utilized as broad spectrum antimicrobials effective against, for example, gram-positive, gram-negative and acid-fast bacteria. Susceptible microorganisms include *Escherichia* spp., *Haemohilus* spp., *Listeria* spp., *Pseudomonas* spp., *Nocardia* spp., *Yersinia* spp., *Klebsiella* spp., *Enterobacter* spp., *Salmonella* spp., *Staphyloccocus* spp., *Streptococcus* spp., *Mycobacteria* spp., *Shigella* spp., and *Serratia* spp. Nonetheless, the aminoglycosides are used primarily to treat infections caused by gram-negative bacteria and, for instance, in combination with penicillins for the synergistic effects. As implied by the generic name for the family, all the aminoglycoside antibiotics contain aminosugars in glycosidic linkage. Ototoxicity is a dose-limiting side-effect of antibiotic administration. For example, nearly 75% of patients given 2 grams of streptomycin daily for 60 to 120 days displayed some vestibular impairment, whereas at 1 gram per day, the incidence decreased to 25% (U.S. Pat. No. 5,059,591). Ototoxicity is also a serious dose-limiting side-effect for cisplatin, a platinum coordination complex, that has proven effective on a variety of human cancers including testicular, ovarian, bladder, and head and neck cancer. Cisplatin damages vestibular systems (Fleischman et al., 1975; Stadnicki et al., 1975; Nakai et al., 1982; Carenza et al., 1986; Sera et al., 1987; Hinojosa and Lerner, 1987; Bareggi et al., 1990).

Accordingly, there exists a need for means to prevent, reduce or treat the incidence and/or severity of ototoxin-induced balance impairment related to vestibular neurons, particularly that arising as an unwanted side-effect of ototoxic therapeutic drugs, which include cisplatin and its analogs and aminoglycoside antibiotics. In addition, there exits a need for methods that allow higher and thus more effective dosing with these ototoxicity-inducing balance-impairing therapeutic drugs by concomitantly preventing or reducing the ototoxic effects of these drugs. What is needed is a method that provides a safe, effective, and prolonged means for prophylactic or curative treatment of ototoxin-induced balance impairment. In addition there is needed a rapid, reliable, and facile system for testing the effects and mechanisms of ototoxins on balance in animals, including humans, and for testing the efficacy of therapeutics to prevent, reduce or treat these impairments. The present invention provides such methods and systems to achieve these goals and others as well.

SUMMARY

The present invention results from the discovery disclosed herein that administration of certain neurotrophins can prevent or reduce gentamicin- and cisplatin-induced cell death of vestibular ganglion neurons in dissociated cell culture in a dose-dependent manner. When neurotrophins or other growth factors were added together with cisplatin or gentamicin to a VGN culture, VGNs were specifically protected by neurotrophin-4/5 (NT-4/5), brain-derived neurotrophic factor (BDNF) and neurotrophin-3 (NT-3), but not by NGF or other growth factors, including epidermal growth factor (EGF), basic fibroblast growth factor (βFGF), and insulin-like growth factor-1 (IGF-1). It is one object of the invention to provide a method for treating a mammal to prevent, reduce, or treat the incidence of or severity of an neuron-related balance impairment, particularly an ototoxin-induced or -inducible balance impairment, by administering to a mammal in need of such treatment a trkB or trkC agonist composition containing a prophylactically or therapeutically effective amount of trkB or trkC agonist. The trkB or trkC agonist is preferably a neurotrophin, more preferably NT-4/5, NT-3, or BDNF, and most preferably NT-4/5, or a functional fragment or derivative thereof, a chimeric neurotrophin, a pantropic neurotrophin, or a small molecule or antibody agonist thereof.

According to the method of this invention a composition of the invention can be administered at a suitable interval(s) either prior to, subsequent to, or substantially concurrently with the administration of or exposure to balance-impairment inducing neuronal damage, preferably ototoxin-induced or -inducible balance impairment. It is another object of the invention to provide a method for treating a mammal to prevent, reduce, or treat neuronal-damage-related balance impairments, preferably an ototoxin-induced balance impairment, by administering to a mammal in need of such treatment a composition containing a prophylactically or therapeutically effective amount of the trkB or trkC agonist in combination with a prophylactically or therapeutically effective amount of a second trkB or trkC agonist or an agent that acts synergistically or additively to enhance or complement the prophylactic or therapeutic effect of the first trkB or trkC agonist.

It is another object of the invention to provide an improved composition containing an ototoxicity-reducing or -preventing effective amount of the trkB or trkC agonist in combination with an ototoxic balance-impairment inducing pharmaceutical drug for administration to a mammal.

Such improved compositions can further contain a pharmaceutically acceptable carrier. The pharmaceutical composition will have lower ototoxicity than the ototoxic pharmaceutical alone, and preferably, have a higher dosage of the ototoxic pharmaceutical than typically used. Examples of such improved compositions include cisplatin or other ototoxic cancer agents or an aminoglycoside antibiotic(s) in combination with a trkB or trkC agonist.

Still further, the invention relates to the use in medicine of compositions of the invention in cases of bacterial infection. The present invention provides a solution to the art that has long sought a therapy and a medicament which can prevent, reduce or treat the ototoxic balance impairment effects currently associated with certain antibiotics, and particularly with the more popular and commonly used aminoglycoside antibiotics without sacrificing the antimicrobial effectiveness of the aminoglycosides.

Still further, the invention relates to the use in medicine of compositions of the invention in cases of cancer. The present invention provides a solution to the art that has long sought a therapy and a medicament which can prevent, reduce, or treat the ototoxic balance impairment effects currently associated with certain chemotherapeutics, and particularly with the more popular and commonly used cisplatin chemotherapeutics without sacrificing the antineoplastic effectiveness of cisplatin or its analogs.

Still further, the invention relates to the use in medicine of compositions of the invention in cases where diuretics are needed. The present invention provides a solution to the art that has long sought a therapy and a medicament which can prevent, reduce, or treat the ototoxic balance impairment effects currently associated with certain diuretics, and particular with the more popular and commonly used loop-diuretics, without sacrificing their diuretic effectiveness.

Finally, it is an object of the invention to provide a organotypic utricle explant culture system that allows reliable, rapid, and facile determination of the ototoxic effect of compounds and the prophylactic or therapeutic effect of candidate compositions and methods of the invention.

Additional objects and features of the invention will be apparent to those skilled in the art from the following detailed description and appended claims when taken in conjunction with the figures.

VGNs were prepared from P5 rats and kept for 2 days in serum-free medium without or with different neurotrophins or other growth factors at a concentration of 10 ng/ml. Quantitation of viable VGNs was done in the same way as in FIG. 2 and the error bars represent SEM. When compared to control cultures, NT-3, BDNF and NT-4/5 all showed very significant survival promoting effects ($p<0.001$) In contrast, NGF, EGF, βFGF and IGF-1 did not produce significant effects ($p>0.05$). The difference in effectiveness between NT-3 and NT-4/5 or BDNF was significant ($p<0.05$).

Figure 2:
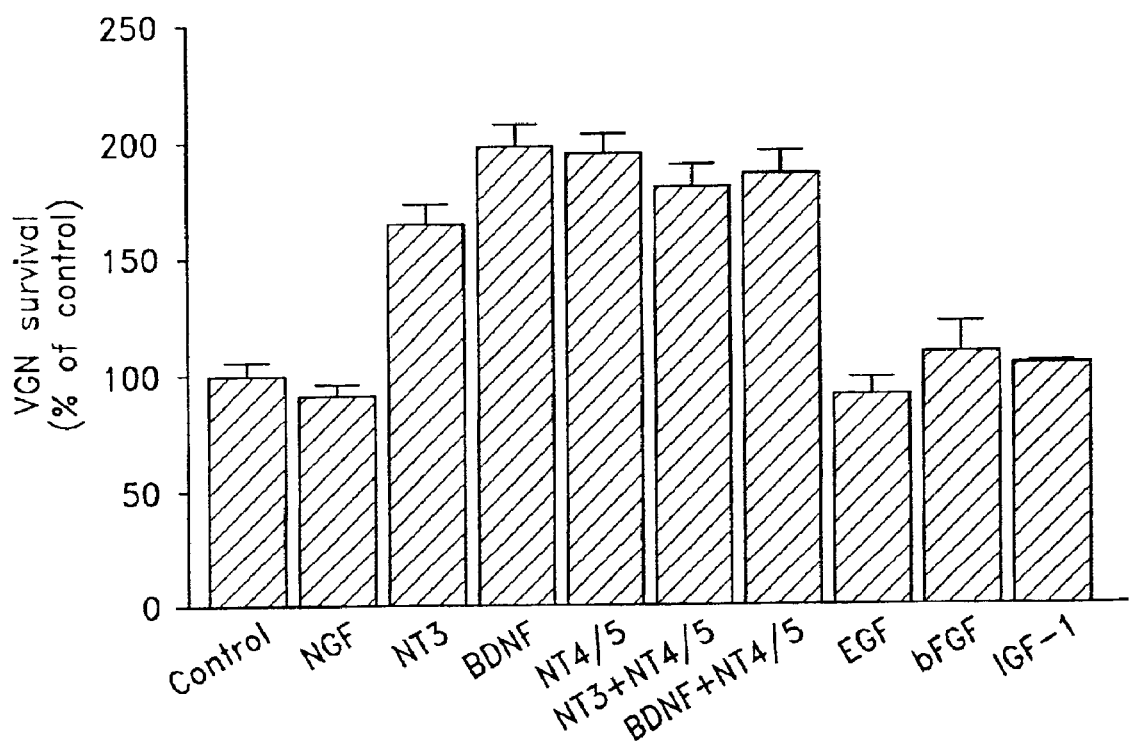
FIG. 2 is a histogram depicting the effects of neurotrophic factors on VGN survival.
Figure 3:
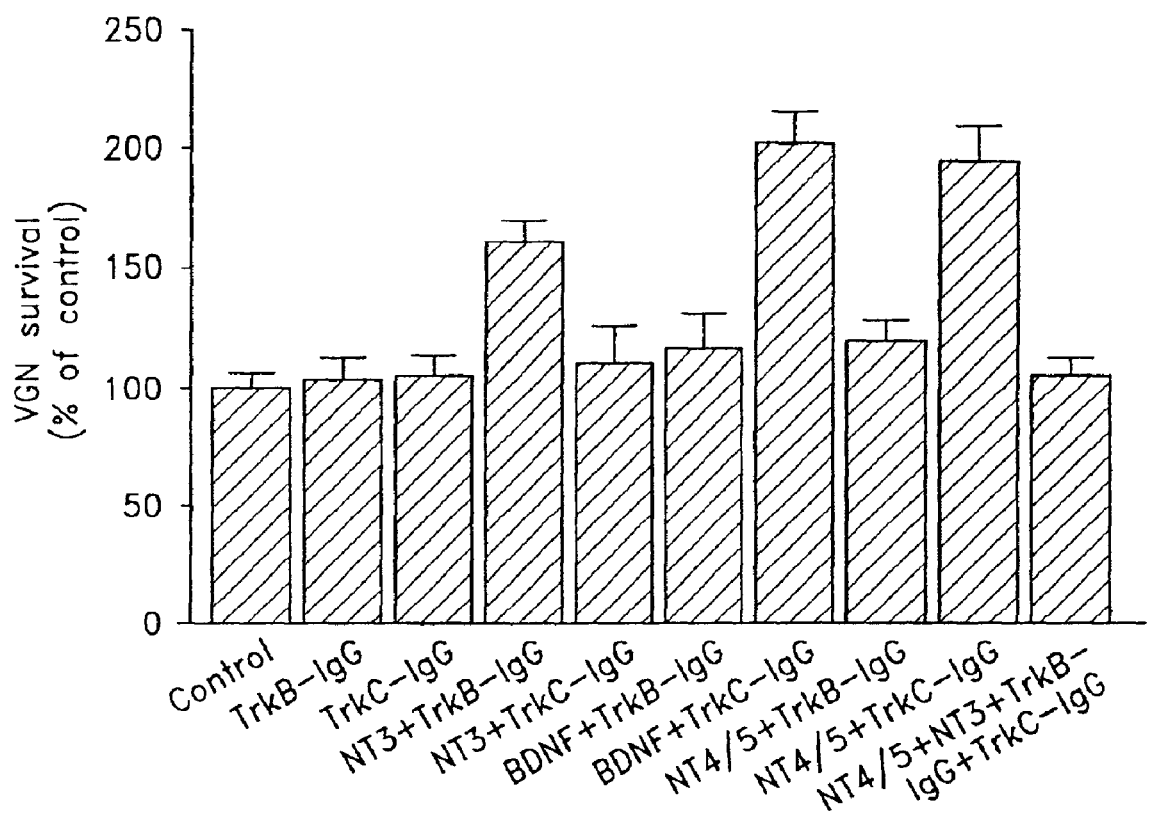

FIG. 3 trkB-IgG and trkC-IgG inhibit the survival-promoting activity of NT-4/5 or BDNF and NT-3, respectively. VGNs were prepared from P5 rats and exposed for 2 days to serum-free medium containing 1 $\mu$g/ml trkB-IgG or trkC-IgG alone or along with different neurotrophins at 10 ng/ml. Quantitation of viable VGNs was done in the same way as in FIG. 2 and the error bars are SEM.

Figure 4:
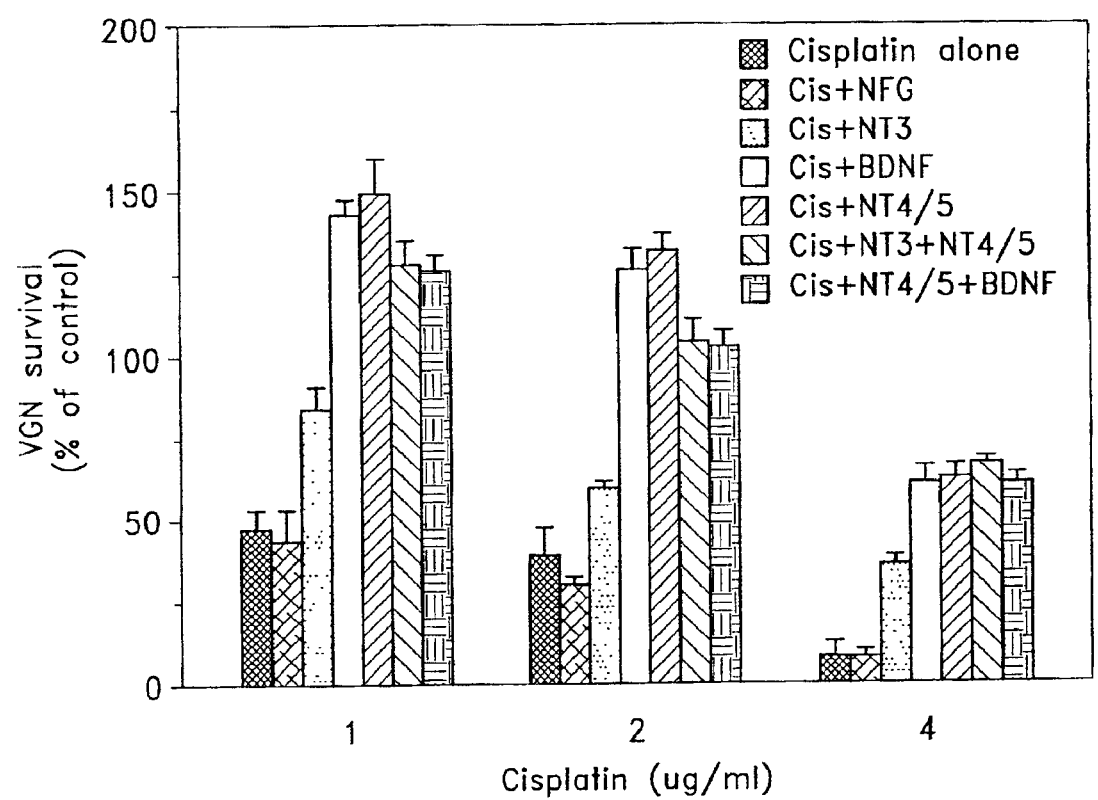

FIG. 4 is a histogram depicting NT-4/5, BDNF and NT-3 protection of VGNs from cisplatin neurotoxicity. VGNs were prepared from P5 rats and maintained for 2 days in serum-free medium containing 1, 2 or 4 $\mu$g/ml of cisplatin alone or together with 10 ng/ml of different neurotrophins. Quantitation of viable VGNs was done in the same way as in FIG. 2. In some cultures in which high concentrations of the ototoxin were added, cell counts were performed from the entire area of the LabTek culture wells as overall number of viable neurons was low. In these experiments cell counts were performed in the same way for control cultures. Data were collected from triplet cultures, and normalized as a percentage of the number of viable VGNs in the control cultures in each of the experiments. The error bars stand for SEM. As compared to the culture containing cisplatin alone, NT-3, BDNF and NT-4/5 all showed very significant protecting effects at all three doses ($p<0.001$). While neuroprotection by NT-4/5 and BDNF was statistically equivalent, the difference between cultures containing NT-3 and cultures containing NT-4/5 (or BDNF) was highly significant ($p<0.001$). Abbreviation: Cis, Cisplatin.

Figure 5:
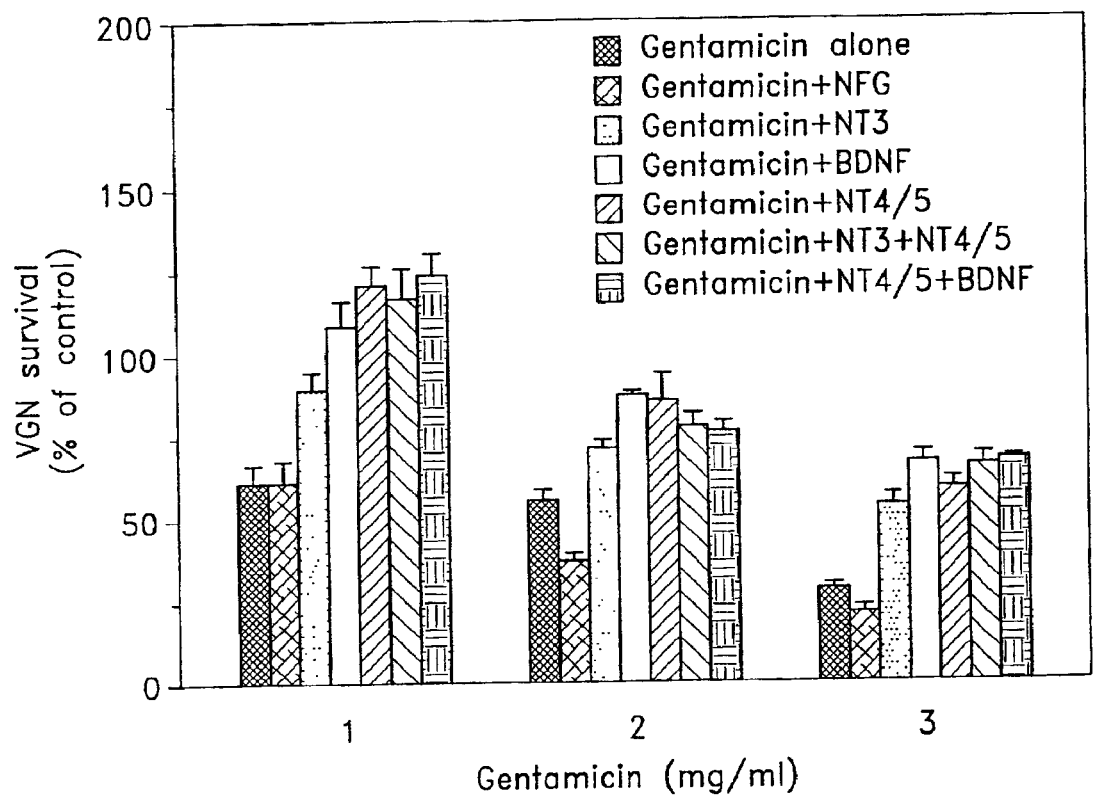

FIG. 5 is a histogram depicting NT-4/5, BDNF and NT-3 protection of VGNs against gentamicin neurotoxicity. VGNs were prepared from P5 rats and maintained for 2 days in serum-free medium containing 1, 2 or 3 mg/ml of gentamicin alone or combined with 10 ng/ml of different neurotrophins. Quantitation of viable VGNs was done in the same way as in FIG. 4. Error bars are SEM. As compared to the culture containing gentamicin alone, NT-3, BDNF and NT-4/5 all showed very significant protective effects at all three doses of gentamicin ($p<0.001$). No significant difference was found between the protective effect of NT-3 against gentamicin and that of NT-4/5 (or BDNF) except for the cultures containing 1 mg/ml of gentamicin ($p<0.05$).

DETAILED DESCRIPTION OF THE PREFERRED EMBODIMENTS

In general, the following words or phrases have the indicated definition when used in the description, examples, and claims:

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

"Treatment" refers to both therapeutic treatment and prophylactic or preventative measures, wherein the object is to prevent or slow down (lessen) neuron-damage-related balance impairment, preferably ototoxin-induced or inducible. Those in need of treatment include those already experiencing a balance impairment, those prone to having the impairment, and those in which the impairments are to be prevented. The balance impairments are due to neuronal damage, preferably ototoxicity, wherein the damage is caused by infections, mechanical injury, loud sounds, aging, or chemical-induced ototoxicity, wherein in the case of ototoxins includes therapeutic drugs including antineoplastic agents, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxic agent" in the context of the present invention is meant a substance that through its chemical action injures, impairs, or inhibits the activity of a component of the nervous system related to balance. The list of ototoxic agents that cause balance impairments includes, but is not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillin or chloramphenicol, or megadoses of vitamins A, D, or B6. Other toxic agents can cause ototoxicity-inducing balance impairment can be characterized by methods as taught herein. By "exposure to an ototoxic agent" is meant that the ototoxic agent is made available to, or comes into contact with, a mammal. Exposure to a toxic agent can occur by direct administration, e g., by ingestion or administration of a food, medicinal, or therapeutic agent, e.g., a chemotherapeutic agent, by accidental contamination, or by environmental exposure, e.g., aerial or aqueous exposure.

"Chronic" administration refers to administration of the agent(s) in a continuous mode as opposed to an acute mode, so as to maintain the initial anti-ototoxic effect for an extended period of time.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

A "patient" for the purposes of the present invention includes both humans and other mammals. Thus the methods are applicable to both human therapy and veterinary applications.

By "balance impairment" is meant a neurologic disorder, oto-neurological, in which the patient displays, complains of, or is diagnosed to have known diagnostic symptoms of a balance disorder, including ataxic gait, preferably grossly ataxic, inability to stand on one leg, or inability to walk heel-to-toe, inability to tandem walk, and dizziness or vertigo that are neurologically related. During vertigo the patient may experience a subjective impression of movement in space (subjective vertigo) or of objects moving in space (objective vertigo) usually with a loss of equilibrium. These impairments of interest to the present invention are those typically associated with damage to neurons, and possibly hair cells, of the vestibular system related to the 8th cranial nerve. Particularly affected may be neurons of the vestibule, semicircular canal, 8th nerve, vestibular neurons of the brainstem and their temporal lobe connections, and more particularly the organ of Corti.

Ototoxicity-related balance impairments include Meniere's syndrome, myringitis, otitis media, acute vestibular neuronitis, herpes zoster oticus, labyrinthitis, middle ear or labyrinthe tumors, petrositis, and otosclerosis. Incorporated herein by reference is Chapters 196, 197, 198 and 199 of The Merck Index, 14th Edition, (1982), Merck Sharp & Dome Research Laboratories, N.J.) relating to description and diagnosis of oto-neurological balance impairments.

Balance impairments include patients diagnosed with vestibular neuronitis. Tests are known and available for diagnosing balance impairments, such as vestibular problems, susceptible to the treatment disclosed herein. Neuro-otological, neuro-ophthalmological, neurological examinations, and electro-oculography can be used. (Wennmo et al. *Acta Otolaryngol* (1982) 94:507–15).

Sensitive and specific measures are available to identify patients with vestibular impairments. Dynamic and static platform posturography can be used for detecting vestibular disorders. The sensory organization test (SOT) of dynamic posturography (EquiTest), the motor "perturbation" test, and Romberg's tests on a static (fixed) force platform each had over 90% specificity. The sensitivity of the SOT was evaluated across five studies involving a total of 836 patients with peripheral vestibular deficits (PVDs). Abnormalities in the SOT were detected in only 40% (n=338) of the cases. Static platform posturography sensitivity was evaluated across six studies involving a total of 571 patients with PVDs, and abnormalities were detected in 53% (n=302) of these cases. Tests of spontaneous and positional nystagmus and the horizontal component of the vestibuloocular reflex (VOR), by comparison, detected PVDs in 48% of 798 patients with suspected vestibular impairment. For patients with vestibular deficits associated with central nervous system disease, a total of 389 cases were identified in five studies and SOT abnormalities were found in 54% (n=209) of these cases. The motor perturbation test was abnormal in 35% (n=41) of 119 patients with central vestibular disease. In conclusion, the sensitivity of static posturography appeared to be slightly better than that of dynamic posturography for detecting PVDs, but the level of sensitivity for each posturography test, as well as for tests of horizontal VOR function, was considered to be low. Combining either type of posturography with other tests of vestibular function, however, increased the overall sensitivity of detecting vestibular deficits to 61% to 89%. It was concluded that dynamic and static platform posturography as well as tests of VOR function lack adequate sensitivity to detect vestibular impairment when applied in isolation. Posturography appears to detect vestibular deficits in some patients who had normal VOR assessments and, therefore, provides supplemental rather than redundant information about vestibular dysfunction.

(Di Fabio, Phys. Ther.(1995) 75:290–305).

In one embodiment the invention constitutes a method for treating a mammal having or prone to a balance impairment or treating a mammal prophylactically to prevent or reduce the occurrence or severity of a balance impairment that would result from exposure to an neuronal injury, loss, or degeneration, preferably caused by an ototoxic agent, wherein a therapeutically effective amount of a trkB or trkC agonist is administered to the mammal. Preferably the agonist is a neurotrophin, more preferably neurotrophin NT-4/5, NT-3, or BDNF, a functional fragment, fusion or derivative thereof, such as a chimeric neurotrophin (having both trkB and trkC agonsim), a pantropic neurotrophin, or a small molecule or antibody agonist thereof, as discussed in detail herein. Most preferably the agonist is NT-4/5 or a chimeric or pantropic variant thereof having at least both trkB and trkC agonist activity. A preferred chimeric or pantropic neurotrophin has a region conferring NT-3-receptor binding specificity and a region conferring NT-4/5-receptor binding specificity. A preferred pantropic neurotrophin is MNTS-1. In a preferred embodiment the binding of a chimeric or pantropic neurotrophin to a neurotrophic receptor is at least 80% of the binding of the natural neurotrophin ligand to the receptor. When the patient is human, the neurotrophins are preferably human neurotrophins or derived from human neurotrophin sequences, in part to avoid or minimize recognition of the agonist as foreign. Optionally, the trkB or trkC agonist is administered alone or in combination. Additional optional components include a hair cell growth factor or agonist, which are compounds known to promote hair cell survival or prevent or reduce cytotoxicity of hair cells. The method of the invention are particularly effective when the balance impairment is ototoxin induced or inducible. Preferably the neurons effected are vestibular ganglion neurons, preferably of Type I.

In one embodiment is a method for treating wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods of the invention are particularly effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

Balance impairments induced by aminoglycosides can be prevented or reduced by the methods of the invention. Although the aminoglycosides are particularly useful due to their rapid bactericidal action in infections by susceptible organisms, their use is limited to more severe, complicated infections because of ototoxic and nephrotoxic side-effects. For this reason the aminoglycosides are considered to have a low therapeutic/risk ratio compared to other antibiotics used systemically. Aminoglycosides are a class of compounds characterized by the ability to interfere with protein synthesis in micro-organisms. Aminoglycosides consist of two or more amino sugars joined in a glycoside linkage to a hexose (or aminocyclitol) nucleus. The hexose nuclei thus far known are either streptidine or 2-deoxystreptamine, though others may be anticipated. Aminoglycoside families are distinguished by the amino sugar attached to the aminocyclitol. For example, the neomycin family comprises three amino sugars attached to the central 2-deoxystreptamine. The kanamycin and glutamicin families have only two amino sugars attached to the aminocyclitol. Aminoglycosides include: neomycins (e.g. neomycin B and analogs and derivatives thereof), paromomycin, ribostamycin, lividomycin, kanamycins (e.g. kanamycin A, kanamycin B, and analogs and derivatives thereof), amikacin, tobramycin, viomycin, gentamicin (e.g., gentamicin C1, gentamicin C 1a, gentamicin C2, and analogs and derivatives thereof), sisomicin, netilmicin, streptomycin, dibekacin, fortimicin, and dihydrostreptomycin.

The aminoglycoside antibiotic which can be employed in conjunction with the ototoxicity inhibiting compositions of the invention is any aminoglycoside antibiotic. Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), streptomycin (Merck Index 9th ed. #8611/8612), paromomycin (Merck Index 9th ed. #6844), sisomicin (Merck Index 9th ed. #8292), isepamicin and netilmicin, all known in the art. The useful antibiotics include the several structural variants of the above compounds (e.g. kanamycin A, B and C; gentamicin A, C1, C 1a, C2 and D; neomycin B and C and the like). The free bases, as well as pharmaceutically acceptable acid addition salts of these aminoglycoside antibiotics, can be employed.

For the purpose of this disclosure, the terms "pharmaceutically acceptable acid addition salt" shall mean a mono or poly salt formed by the interaction of one molecule of the aminoglycoside antibiotic with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals.

Accordingly, the methods and compositions of the invention find use for the prevention and treatment of opportunistic infections in animals and man which are immunosuppressed as a result of either congenital or acquired immunodeficiency or as a side-effect of chemotherapeutic treatment. According to an alternate embodiment of the present invention, a trkB or trkC agonists is used advantageously in combination with a known antimicrobial agent to provide improved methods and compositions to prevent and/or treat diseases induced by gram positive bacteria including, but not limited to: *Staphylococcus aureus, Streptococcus pneumonia, Hemophilus influenza*; gram negative bacteria including, but not limited to: *Escherichia coli; Bacterium enteritis, Francisella tularensis;* acid-fast bacteria including, but not limited to *Mycobacterium tuberculosis,* and *Mycobacterium leprae.* Use of a combination of an antimicrobial agent together with a trkB or trkC agonist is advantageous with antibacterial aminoglycosides such as gentamicin, streptomycin, and the like which are known to have serious ototoxicity, which reduce the usefulness of such antimicrobial agents. Use of trkB or trkC agonist in combination with such agents permits a lower dosage of the toxic antimicrobial agents while still achieving therapeutic (antibacterial) effectiveness.

In some embodiments the trkB or trkC agonist is co-administered with an ototoxin. For example, an improved method is provided for treatment of infection of a mammal by administration of an aminoglycoside antibiotic, the improvement comprising administering a therapeutically effective amount of a trkB or trkC agonist to the patient in need of such treatment to reduce or prevent ototoxin-induced balance impairment associated with the antibiotic. In yet another embodiment is provided an improved method for treatment of cancer in a mammal by administration of a chemotherapeutic compound, the improvement comprises administering a therapeutically effective amount of a trkB or trkC agonist to the patient in need of such treatment to reduce or prevent ototoxin-induced balance impairment associated with the chemotherapeutic drug.

Also provided herein are methods for promoting vestibular ganglion neuron survival upon, prior to, or after exposure to an agent or effect that is capable of inducing a neuronal-injury-related balance impairment. Such agents and effects are those described herein. The method includes the step of administering to the neuron an effective amount of trkB or trkC agonist or other such compositions as discussed herein. Preferably, the method is used upon, prior to, or after exposure to a balance-impairing ototoxin.

In another preferred embodiment the ototoxic agent is a chemotherapeutic agent, an antineoplastic agent. Preferred agents include but are not limited to cisplatin or cisplatin-like compounds Balance impairments resulting from the administration of chemotherapeutic agents can be prevented or reduced by the methods of the invention. Ototoxic chemotherapeutic agents amenable to the methods of the invention include, but are not limited to, cisplatin, taxol, and other chemotherapeutic agents believed to cause ototoxin-induced balance impairments, e.g., vincristine, an antineoplastic drug used to treat hematological malignancies and sarcomas. The ototoxicity is dose-related.

Balance impairments resulting from administration of diuretics can be prevented or reduced by the methods of the invention. Diuretics, particularly "loop" diuretics, i.e. those that act primarily in the Loop of Henle, are candidate ototoxins. Illustrative examples, not limiting to the invention method, include furosemide, ethacrynic acid, and mercurial. Diuretics are typically used to prevent or eliminate edema. Diuretics are also used in nonedematous states such as hypertension, hypercalcemia, idiopathic hypercalciuria, and nephrogenic diabetes insipidus.

In one embodiment the trkB or trkC agonist is administered prior to administration or exposure to a balance-impairing event such as exposure to an ototoxin.

In another embodiment the trkB or trkC agonist is administered with an agent that promotes hair cell growth or regeneration.

Preparation and Identification of Agonists

Agonists to trkB or trkC can be prepared by using the known family of ligands for trkB or trkC. Survival of developing sensory neurons is dependent upon trophic factors derived from their target tissues (Davies et al., 1986). Generally, a neurotrophin is a protein involved in the development, regulation and maintenance of the nervous system, and in particular of neurons. Currently, there are at least five known important neurotrophic factors: nerve growth factor (NGF), neurotrophin-3 (NT-3), neurotrophin-4 (NT-4/5, also sometimes called neurotrophin-5 (NT-5) or NT-4/5), brain-derived neurotrophic factor (BDNF), and ciliary neurotrophic factor (CNTF). The best characterized mammalian neurotrophic factors are members of the nerve growth factor (NGF) family of proteins, and are called neurotrophins. These include NGF (Levi-Montalcini, 1987), brain-derived neurotrophic factor (BDNF) (Barde et al., 1982; Leibrock et al., *Nature* (1989) 341:149) neurotrophin-3 (NT-3) (Hohn et al., Nature, 344: 339 (1990); Maisonpierre et al., Science, 247: 1446 (1990); Rosenthal et al., Neuron, 4: 767 (1990); copending U.S. Ser. No. 07/494,024 filed Mar. 15, 1990; U.S. application Ser. No. 07/490,004, filed Mar. 7, 1990; Ernfors et al., 1990; Jones and Reichardt, 1990) and neurotrophin-4/5 (NT-4/5) (Berkemeier et al., 1991; Ip et al., 1992) and neurotrophin-6 (NT-6). While NT-6 is newly cloned from *Xenopus* (Gotz et al., 1994) and is less well understood, it is now well accepted that the other four mammalian neurotrophins exert their biological functions through activation of high-affinity binding receptors, the trks (Barbacid, 1993; Snider, 1994). Each of the neurotrophins binds to specific high-affinity receptors, the trks (Klein et al., 1990; Kaplan et al., 1991; Klein et al., 1991a; Klein et al., 1991b; Soppet et al., 1991; Squinto et al., 1991; Lamballe et al., 1991; Tsoulfas et al., 1993; Ip et al., 1993). For example, NGF selectively binds to trkA, BDNF and NT-4/5 to trkB, and NT-3 to trkC. Although neurotrophins exert their main effects through binding to the trks, they also bind to the NGF low affinity receptor, P75. Recent studies indicate that the binding of NGF to P75 may enhance the trkA-mediated signal transduction pathway (Davies et al., 1993a; Verdi et al., 1994; Barker and Shooter, 1994; Clary and Reichardt, 1994).

Neurotrophins transduce intracellular signalling at least in part through the ligand-dependent activation of a class of tyrosine kinase-containing receptors of $M_r=140–145,000$ known as the trks (Martin-Zanca, et al. (1989); Kaplan, et al. (1991) Nature; Klein, et al.(1991a); Kaplan, et al. (1991) Science); Klein, et al. (1991b) Cell; Soppet, et al. (1991); Squinto, et al. (1991); Lamballe, et al. (1991); Tsoulfas, et al. (1993)). Thus, the signal transduction pathway of neurotrophins is initiated by this high-affinity binding to and activation of specific tyrosine kinase receptors and subsequent receptor autophosphorylation (Cordon-Cardo, et al. (1991)). Although there is some degree of cross-receptor interaction between the neurotrophins and the different trks, the predominant specificity appears to be NGF/trkA, BDNF/trkB, and NT-3/trkC while NT-4/5 appears to interact primarily with trkB as efficiently as BDNF (see above and Klein, et al. (1992); Klein, et al. (1989)).

Expression of trkB, trkC and p75 mRNAs in embryonic cochleovestibular ganglia (Ylikoski et al., 1993; Schecterson and Bothwell, 1994) and BDNF and NT-3 mRNAs in the inner ear structures (Pirvola et al., 1992; Wheeler et al., 1994; Schecterson and Bothwell, 1994) suggest a possible role of neurotrophins in the development of VGNs and maintenance of VGNs in the adult. However, the expression of neurotrophin receptors at the protein level has not been well determined and the effects of the four neurotrophins have not been carefully compared on VGNs. For example, the effects of NT-4/5 on the survival of postnatal VGNs have not been studied. In the present application, immunohistochemical evidence demonstrates that VGNs make trkB and p75, but not trkA proteins. Addition of NT-4/5, BDNF or NT-3 to the cultures enhanced postnatal rat VGN survival. In contrast, NGF showed no detectable effects on survival of VGNs. The survival-promoting effects of NT-4/5 (or BDNF) and NT-3 were specifically abolished by their specific antagonists trkB-IgG and trkC-IgG fusion proteins (Shelton et al., 1995), respectively. Furthermore, evidence presented herein demonstrates that ototoxins including cisplatin and gentamicin induced cell death of VGNs in normal cultures in a dose-dependent manner and that NT-4/5, BDNF and NT-3, but not NGF, prevented or reduced these neurotoxic effects.

In situ hybridization studies indicate that mRNAs for trkB and trkC are expressed by embryonic cochleovestibular ganglia (Ylikoski et al., 1993; Schecterson and Bothwell, 1994) and that mRNAs for BDNF and NT-3 are found in the inner ear including organ of Corti (Pirvola et al., 1992; Wheeler et al., 1994; Schecterson and Bothwell, 1994). However, the expression patterns of neurotrophin receptors have not been well determined at the protein level and no study has compared the biological effects of the four neurotrophins on VGNs. In particular, the survival-promoting effects of NT-4/5 have not been tested on VGNs.

DNA sequences encoding NGF, BDNF and NT-3 have all been isolated (ullrich et al., Nature 303:821–825; Hyman et al., WO 91/03568; Hohn et al., WO 91/03569; and Kaisho et al., FEBS Letters 266:187–191). Researchers have transformed animal and non-animal hosts with these sequences in order to express the neurotrophins.

Researchers have expressed human NGF, BDNF and NT-3 in mammalian expression systems. Bruce and Heinrich (1989, Neurobiology of Aging 10:89–94) expressed a DNA sequence encoding the complete precursor for hNGF in COS cells and detected hNGF dimer in the conditioned medium. However, they could not determine the efficiency at which pre-pro-hNGF was converted to mature hNGF. Kakinuma et al (EP 0 414 151, 1991) expressed active hNGF in CHO cells. Hyman et al. (WO 91/03568, 1991) expressed hBDNF in CHO cells. Nakahama et al. (EP 0 386 752, 1990) and Hohn et al. (WO 91/03569, 1991) expressed hNT-3 in COS cells.

U.S. Pat. Nos. 5,235,043 and 5,229,500 disclose human BDNF sequence and methods for its production and formulation. U.S. patent application Ser. No. 08/583,330, identified as, and U.S. patent application Ser. No. 08/779,357, identified as, and each entitled "Treatment of Hearing Impairments" is also incorporated herein by reference.

NT-4/5, and its chimeric or pantropic neurotrophins, are most preferred agonists for use in the methods and compositions of the present invention. Its human gene and amino acid sequence are known (U.S. Pat. No. 5,364,769, which is incorporated herein by reference). NT-4/5 is defined to be a polypeptide encoded by the known mature human NT-4/5 nucleotide sequence set forth in U.S. Pat. No. 5,364,769, fragments thereof having greater than about 5 residues comprising an immune epitope or other biologically active site of NT-4/5, amino acid sequence variants of said sequence, wherein an amino acid residue has been inserted N- or C-terminal to, or within, said sequence or its fragment as defined above, and/or amino acid sequence variants of said sequence or its fragment as defined above wherein an amino acid residue of said sequence or fragment thereof has been substituted by another residue, including other animal species of NT-4/5 such as rat preproNT-4/5, and derivatives of NT-4/5 or its fragments as defined above wherein the NT-4/5 or its fragments have been covalently modified by substitution with a moiety other than a naturally occurring amino acid; provided, however, that such fragment or variant is novel and unobvious over the prior art, and is not NGF, BDNF, or NT-3 of any animal species or any known fragment of such NGF, BDNF, or NT-3. Mature NT-4/5 amino acid sequence variants generally will be about 75% (and usually >85%) homologous on an identical residue basis after aligning (introducing any necessary spaces) to provide maximum homology.

NT-4/5 nucleic acid is defined as RNA or DNA which encodes a NT-4/5 polypeptide or which hybridizes to such DNA and remains stably bound to it under stringent conditions and is greater than about 10 bases in length; provided, however, that such hybridizing nucleic acid is novel and unobvious over any prior art nucleic acid including that which encodes or is complementary to nucleic acid encoding BDNF, NT-3, or NGF. Stringent conditions are those which (1) employ low ionic strength and high temperature for washing, for example, 0.15 M NaCl/0.015 M sodium citrate/ 0.1% NaDodSO$_4$ at 50° C., or (2) use during washing a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

DNA encoding NT-4/5 is obtained from brain tissue cDNA libraries, or genomic DNA, or by in vitro synthesis. Hybridizing nucleic acid generally is obtained by in vitro synthesis. Identification of NT-4/5 DNA most conveniently is accomplished by probing human cDNA or genomic libraries by labeled oligonucleotide sequences selected from the known sequence in accord with known criteria, among which is that the sequence should be of sufficient length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. The nucleic acid may be labeled for diagnostic purposes.

Amino acid sequence variants of NT-4/5 are prepared by introducing appropriate nucleotide changes into the NT-4/5 DNA, or by in vitro synthesis of the desired NT-4/5. Such variants include, for example, deletions from, or insertions or substitutions of, residues within the amino acid sequence for human NT-4/5. Any combination of deletion, insertion, and substitution is made to arrive at the final construct, provided that the final construct possesses the desired characteristics. The amino acid changes also may result in further modifications of NT-4/5 upon expression in recombinant hosts, e.g. introducing or moving sites of glycosylation, or introducing membrane anchor sequences (in accordance with U.S. Ser. No. 07/083,757, filed Aug. 6, 1987, which is equivalent to PCT WO 89101041 published Feb. 9, 1989).

There are two principal variables in the construction of amino acid sequence variants: the location of the mutation site and the nature of the mutation. These are variants may represent naturally occurring alleles (which will not require manipulation of the NT-4/5 DNA) or predetermined mutant forms which are made by mutating the DNA, either to arrive at an allele or a variant that is not found in nature. In general, the location and nature of the mutation chosen will depend upon the NT-4/5 characteristic to be modified. For example, candidate NT-4/5 antagonists or super agonists will be initially selected by locating sites that are identical or highly conserved among NGF, BDNF, NT-3, and NT-4/5. These sites then will be modified in series, e.g., by (1) substituting first with conservative choices and then with more radical selections depending upon the results achieved, (2) deleting the target residue, or (3) inserting residues of the same or different class adjacent to the located site, or combinations of options 1–3.

One helpful technique is called "ala scanning". Here, a residue or group of target residues 3.0 are identified and substituted by alanine or polyalanine. Those domains demonstrating functional sensitivity to the alanine substitutions then are refined by introducing further or other variants at or for the sites of alanine substitution. Obviously, such variations which, for example, convert NT-4/5 into NGF, BDNF, or NT-3 are not included within the scope of this invention, nor are any other NT-4/5 variants or polypeptide sequences that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed NT-4/5 variants are screened for the optimal combination of desired activity.

Amino acid sequence deletions generally range from about 1 to 30 residues, more preferably about 1 to 10 residues, and typically are contiguous. Deletions may be introduced into regions of low homology among BDNF, NGF, NT-3, and NT-4/5 to modify the activity of NT-4/5. Deletions from NT-4/5 in areas of substantial homology with BDNF, NT-3, and NGF will be more likely to modify the biological activity of NT-4/5 more significantly. The number of consecutive deletions will be selected so as to preserve the tertiary structure of NT-4/5 in the affected domain, e.g., beta-pleated sheet or alpha helix.

Amino acid sequence insertions include amino- and/or carboxyl-terminal fusions ranging in length from one residue to polypeptides containing a thousand or more residues, as well as intrasequence insertions of single or multiple amino acid residues. Intrasequence insertions (i.e., insertions within the mature NT-4/5 sequence) may range generally from about 1 to 10 residues, more preferably 1 to 5, most preferably 1 to 3. An example of a terminal insertion includes fusion of a heterologous N-terminal signal sequence to the N-terminus of the NT-4/5 molecule to facilitate the secretion of mature NT-4/5 from recombinant hosts. Such signals generally will be homologous to the intended host cell and include STII or lpp for *E. coli,* alpha factor for yeast, and viral signals such as herpes gD for mammalian cells. Other insertions include the fusion of an immunogenic polypeptide such as a bacterial or yeast protein to the N- or C-termini of NT-4/5.

The third group of variants are those in which at least one amino acid residue in the NT-4/5 molecule, and preferably only one, has been removed and a different residue inserted in its place. In some embodiments substitutions of one to five amino acids are made. In yet another embodiment one to three amino acids are substituted. In some preferred embodiments two amino acid substitutions are made. The substitutions can be chosen from the table herein. An example is the replacement of arginine and lysine by other amino acids to render the NT-4/5 resistant to proteolysis by serine proteases, thereby creating a more stable NT-4/5 analogue. The sites of greatest interest for substitutional mutagenesis include sites where the amino acids found in BDNF, NGF, NT-3, and NT-4/5 are substantially different in terms of side chain bulk, charge or hydrophobicity, but where there also is a high degree of homology at the selected site within various animal analogues of NGF, NT-3, and BDNF (e.g., among all the animal NGFs, all the animal NT-3s, and all the BDNFs). This analysis will highlight residues that may be involved in the differentiation of activity of the trophic factors, and therefore, variants at these sites may affect such activities. Examples of such NT-4/5 sites, numbered from the mature N-terminal end, and exemplary substitutions include NT-4/5 ($G_{78}$-->K, H, Q or R) and NT-4/5 ($R_{85}$-->E, F, P, Y or W). Other sites of interest are those in which the residues are identical among all animal species' BDNF, NGF, NT-3, and NT-4/5, this degree of conformation suggesting importance in achieving biological activity common to all four factors. These sites, especially those falling within a sequence of at least 3 other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg; | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Sites particularly suited for conservative substitutions include, numbered from the N-terminus of the mature NT-4/5, R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118. Cysteine residues not involved in maintaining the proper conformation of NT-4/5 also may be substituted, generally with serine, in order to improve the oxidative stability of the molecule and prevent aberrant crosslinking. Sites other than those set forth in this paragraph are suitable for deletional or insertional studies generally described above.

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another. Such substituted residues also may be introduced into the conservative substitution sites set forth above or, more preferably, into the remaining (non-conserved) sites.

examples of NT-4/5 (SEQ ID NO: 1) variants include NT-4/5(65NAE67-->NAS or NAT) (this adds N-linked glycosylation site); NT-4/5(R83–Q94); NT-4/5(G1–C6 1) (variants so depicted are fragments containing the residues indicated); NT-4/5 (G1–C17); NT-4/5 (C17–C61); NT-4/5 (C17–C78); NT-4/5(C17–C90); NT-4/5(C17–C119); NT-4/5(C17–C 121)/NT-4/5(R11–R27); NT-4/5(R11–R34); NT-4/5(R34–R53); NT-4/5(C61–C78); NT-4/5(R53–C61); NT-4/5(C61–C119); NT-4/5(C61–C78); NT-4/5(C78–C 119); NT-4/5(C61–C90); NT-4/5(R60–C78); NT-4/5(K62–C119); NT-4/5(K62–K91); NT-4/5(R79–R98); NT-4/5(R83–K93); NT-4/5(T101–R111); NT-4/5(G1–C121) V L T V K R V R R (SEQ ID NO: 4); NT-4/5(V40–C121) V L T V K R V R R (SEQ ID NO: 5); NT-4/5(V40–C121) S L T I K R I R A (SEQ ID NO: 6);NT-4/5(V40–C121)T L S R K A G R R A (SEQ ID NO:7);D D D S P I A R R G E I S V C D S V S D W V S A P D K D T A V D I K G D D V M V L K K V G I N H S V (SEQ ID NO: 8); NT-4/5(V40–C121); hNGF(S1–V48) NT-4/5(V40–C121) hNGF(V109–A120); BDNF(R7–Q48) NT-4/5(V40–C121) BDNF(V110–R1119); NT-4/5 (ΔC78); NT-4/5(ΔC61); NT-4/5(ΔQ54–ΔT59) (variants depicted in this fashion comprise deletions of the indicated span of residues, inclusive); NT-4/5(ΔR60–ΔD82); NT-4/5(ΔH85–ΔS88); NT-4/5(ΔW86–ΔT101); NT-4/5 (R53-->H); NT-4/5(K91-->H); NT-4/5(V108-->F); NT-4/5 (R84-->Q, H, N, T, Y or W); and NT-4/5(D116-->E, N, Q, Y, S or T).

Also included is NT-4/5 wherein position 70 is substituted with an amino acid residue other than G, E, D, or P; position 71 with other than A, P or M; and/or position 83 with other than R, D, S, or K; as well as cyclized NT-4/5 fragments, including cyclic polypeptides comprising the sequences IKTG (SEQ ID NO: 9); EIKTG (SEQ ID NO: 10), EIKTGN (SEQ ID NO: 11), SPV, SPVK (SEQ ID NO: 12), HQV, KSS, KSSA (SEQ ID NO: 13), YAEHKS (SEQ ID NO: 14), RYAEHKS (SEQ ID NO: 15), RYAEHKSH (SEQ ID NO: 16), YAEHKSH (SEQ ID NO: 17), ANRTS (SEQ ID NO: 18), NRT, ANRT (SEQ ID NO: 19), NRTS (SEQ ID NO: 20), KEA, KEAR (SEQ ID NO: 21), KEARP (SEQ ID NO: 22), IDDK (SEQ ID NO: 23); SENN (SEQ ID NO: 24) TSENN (SEQ ID NO: 25), TSENNK (SEQ ID NO: 26) or KLVG (SEQ ID NO: 27).

Also within the scope hereof are BDNF, NT-3, and NGF amino acid variants having analogous structures to the NT-4/5 variants set forth herein. For example, the analogous positions of NGF, NT-3, and BDNF are substituted with a residue other than D, E, or P, respectively, in analogy to the same mutation at position 70 of NT-4/5.

DNA encoding NT-4/5 variants preferably is prepared by site-specific mutagenesis of DNA that encodes an earlier prepared variant or a nonvariant version of NT-4/5. Site-specific mutagenesis allows the production of NT-4/5 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA, 2: 183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily commercially available and their use is generally well known to those skilled in the art. Also, plasmid vectors that contain a single-stranded phage origin of replication (Veira et al., Meth. Enzymol., 153: 3 [1987]) may be employed to obtain single-stranded DNA. Alternatively, nucleotide substitutions are introduced by synthesizing the appropriate DNA fragment in vitro and amplifying it by polymerase chain reaction (PCR) procedures known per se in the art.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., Proc. Natl. Acad. Sci. (USA), 75: 5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated region may be removed and placed in an appropriate vector for protein production, generally an expression vector of the type that is typically employed for transformation of an appropriate host.

Most deletions and insertions, and substitutions in particular, are not expected to produce radical changes in the characteristics of the NT-4/5 molecule, and single substitutions will preserve at least one immune epitope in the NT-4/5 polypeptide.

Since it is often difficult to predict in advance the characteristics of a variant NT-4/5, it will be appreciated that some screening will be needed to select the optimal variant. One can screen for enhanced trophic activity, differential neuron cell type specificity, stability in recombinant cell culture or in plasma (e.g. against proteolytic cleavage), possession of antagonist activity, oxidative stability, ability to be secreted in elevated yields, and the like. For example, a change in the immunological character of the NT-4/5 molecule, such as affinity for a given antibody, is measured by a competitive-type immunoassay. Changes in the enhancement or suppression of neurotrophic activities by the candidate mutants are measured by dendrite outgrowth or explant cell survival assays. Modifications of such protein properties as redox or thermal stability, hydrophobicity, susceptibility to proteolytic degradation, or the tendency to aggregate with carriers or into multimers are assayed by methods well known in the art.

Trypsin or other protease cleavage sites are identified by inspection of the encoded amino acid sequence for paired basic residues, e.g. combinations of adjacent arginyl and lysinyl residues. These are rendered inactive to protease by substituting one of the residues with another residue, preferably a basic residue such as glutamine or a hydrophobic residue such as serine; by deleting one or both of the basic residues; by inserting a prolyl residue immediately after the last basic residue; or by inserting another residue between the two basic residues.

A variant NT-4/5 typically is made by site-specific mutagenesis of the native NT-4/5-encoding nucleic acid, expression of the variant nucleic acid in recombinant cell culture, and, optionally, purification from the cell culture, for example, by bioassay of the variant's activity or by immunoaffinity adsorption on a rabbit polyclonal anti-NT-4/5 column (to absorb the variant by binding it to at least one remaining immune epitope). Small fragments, on the order of 40 residues or less, are conveniently made by in vitro methods.

The NT-4/5-encoding nucleic acid, whether variant or cDNA, then is ligated into a replicable vector for further cloning or for expression. Vectors are useful for performing two functions in collaboration with compatible host cells (a host-vector system). One function is to facilitate the cloning of the nucleic acid that encodes the NT-4/5, i.e., to produce usable quantities of the nucleic acid. The other function is to direct the expression of NT-4/5. One or both of these functions are performed by the vector-host system. The vectors will contain different components depending upon the function they are to perform as well as the host cell that is selected for cloning or expression.

Each vector will contain nucleic acid that encodes NT-4/5 as described above. Typically, this will be DNA that encodes the NT-4/5 in its mature form linked at its amino terminus to a secretion signal. This secretion signal preferably is the NT-4/5 presequence that normally directs the secretion of NT-4/5 from human cells in vivo. However, suitable secretion signals also include signals from other animal NT-4/5, signals from NGF, NT-2, or NT-3, viral signals, or signals from secreted polypeptides of the same or related species.

If the signal sequence is from another NT molecule, it may be the precursor sequence spanning from the initiating methionine (M) residue of NT-2, NT-3, or NGF up to the arginine (R) residue just before the first amino acid of the mature protein, or a consensus or combination sequence from any two or more of those precursors taking into account homologous regions of the precursors. The DNA for such precursor region is ligated in reading frame to DNA encoding the mature NT-4/5.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the 2 $\mu$plasmid origin for yeast and various viral origins (SV40, polyoma, adenovirus, VSV or BPV) are useful for cloning vectors in mammalian cells. Origins are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in E. coli and then the same vector is transfected into yeast or mammalian cells for expression even though it is not capable of replicating independently of the host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of NT-4/5 DNA. However, the recovery of genomic DNA encoding NT-4/5 is more complex than that of an exogenously replicated vector because restriction enzyme digestion is required to excise the NT-4/5 DNA.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding, D-alanine racemase for bacilli.

A suitable selection gene for use in yeast is the trp1 gene present in the yeast plasmid YRp7 (Stinchcomb et al., 1979, Nature 282:39; Kingsman et al., 1979, Gene 7:141; or Tschemper et al., 1980, Gene 10:157). The trp1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the NT-4/5 nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes NT-4/5. Amplification is the process by which genes in greater demand for the production of a protein critical for growth are reiterated in tandem within the chromosomes of successive generations of recombinant cells. Increased quantities of NT-4/5 are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, Proc. Nat'l. Acad. Sci. USA 77:4216. A particularly useful DHFR is a mutant DHFR that is highly resistant to MTX (EP 117,060A). This selection agent can be used with any otherwise suitable host, e.g. ATCC No. CCL61 CHO-K1, notwithstanding the presence of endogenous DHFR. The DHFR and NT-4/5-encoding DNA then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding NT-4/5, wild-type DHFR, and another selectable marker such as the neo gene can be identified Using a selection agent for the selectable marker such as G418 and then selected and amplified using methotrexate in a wild-type host that contains endogenous DHFR.

Other methods, vectors and host cells suitable for adaptation to the synthesis of NT-4/5 in recombinant vertebrate cell culture are described in M. J. Gething et al., Nature 293:620–625 (1981); N Mantei et al., Nature 281:40–46 (1979); and A. Levinson et al., EP 117,060A and 117,058A. A particularly useful plasmid for mammalian cell culture expression of NT-4/5 is pRK5 (EP pub. no. 307,247) or pSVI6B (U.S. Ser. No. 07/441,574 filed Nov. 22, 1989).

Expression vectors, unlike cloning vectors, should contain a promoter which is recognized by the host organism and is operably linked to the NT-4/5 nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to NT-4/5-encoding DNA by removing them from their gene of origin by restriction enzyme digestion, followed by insertion 5' to the start codon for NT-4/5. This is not to say that the genomic NT-4/5 promoter is not usable. However, heterologous promoters generally will result in greater transcription and higher yields of expressed NT-4/5.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang et al., 1978, Nature 275:615; and Goeddel et al., 1979, Nature 281:544), alkaline phosphatase, a tryptophan (trp) promoter system (Goeddel, 1980, Nucleic Acids Res. 8:4057 and EPO Appln. Publ. No. 36,776) and hybrid promoters such as the tac promoter (H. de Boer et al., 1983, Proc. Nat'l. Acad. Sci. USA 80:21–25). However, other known bacterial promoters are suitable.

Their nucleotide sequences have been published, thereby enabling a skilled worker operably to ligate them to DNA encoding NT-4/5 (Siebenlist et al. 1980, Cell 20:269) using linkers or adaptors to supply any required restriction sites. Promoters for use in bacterial systems also will contain a Shine-Dalgarno (S.D.) sequence operably linked to the DNA encoding NT-4/5.

Suitable promoting sequences for use with yeast hosts include the promoters for 3-phosphoglycerate kinase (Hitzeman et al., 1980, J. Biol. Chem. 255:2073) or other glycolytic enzymes (Hess et al., 1968, J. Adv. Enzyme Reg. 7:149; and Holland, 1978, Biochemistry 17:4900), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

NT-4/5 transcription from vectors in mammalian host cells is controlled by promoters obtained from the genomes of viruses such as polyoma, cytomegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers et al., 1978, Nature 273:113). Of course, promoters from the host cell or related species also are useful herein.

Transcription of NT-4/5-encoding DNA by higher eukaryotes is increased by inserting an enhancer sequence into the vector. An enhancer is a nucleotide sequence, usually about from 10–300 bp, that acts on a promoter to increase its transcription and does so in a manner that is relatively orientation and position independent. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenoviral enhancers. The enhancer may be spliced into the vector at a position 5' or 3' to the NT-4/5-encoding sequence, but is preferably located at a site 5' from the promoter.

Expression vectors used in eukaryotic host cells (yeast, fungi, insect, plant, animal, human or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding NT-4/5. The 3' untranslated regions also include transcription termination sites.

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), pseudomonas species, or *Serratia marcesans* are suitable.

In addition to prokaryotes, eukaryotic microbes such as filamentous fungi or yeast are suitable hosts for NT-4/5-encoding vectors. *Saccharomyces cerevisiae*, or common baker's yeast, is the most commonly used among lower eukaryotic host microorganisms. However, a number of other genera, species and strains are commonly available and useful herein.

Suitable host cells for the expression of NT-4/5 are derived from multicellular organisms. Such host cells are capable of complex processing and glycosylation activities. In principle, any higher eukaryotic cell culture is workable, whether from vertebrate or invertebrate culture, although cells from mammals such as humans are preferred. Propagation of such cells in culture is per se well known. See issue Culture, Academic Press, Kruse and Patterson, editors (1973). Examples of useful mammalian host cell lines are VERO and HeLa cells, Chinese hamster ovary cell lines, the W138, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

Covalent modifications of NT-4/5 molecules are included within the scope of this invention. Variant NT-4/5 fragments having up to about 40 residues may be conveniently prepared by in vitro synthesis. In addition, covalent modifications are introduced into the molecule by reacting targeted amino acid residues of the NT-4/5 polypeptide with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking NT-4/5 to a water-insoluble support matrix or surface for use in the method for purifying anti-NT-4/5 antibodies, and vice versa. Commonly used crosslinking agents include, e g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co, San Francisco, pp. 79–86 [1983]), acetylation of the N-terminal amine, and amidation of any C-terminal carboxyl group. NT-4/5 also is covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

NT-4/5 preferably is recovered from the culture medium as a secreted protein, although it also may be recovered from host cell lysates when directly expressed without a secretory signal. When NT-4/5 is expressed in a recombinant cell other than one of human origin, the NT-4/5 is thus completely free of proteins of human origin. However, it is necessary to purify NT-4/5 from recombinant cell proteins in order to obtain preparations that are substantially homogeneous as to protein. As a first step, the culture medium or lysate is centrifuged to remove particulate cell debris. NT-4/5 thereafter is purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis using, for example, Sephadex G-75. NT-4/5 variants in which residues have been deleted, inserted or substituted are recovered in the same fashion as native NT-4/5, taking account of any substantial changes in properties occasioned by the variation. For example, preparation of an NT-4/5 fusion with another protein, e.g. a bacterial or viral antigen, facilitates purification because an immunoaffinity column containing antibody to the antigen can be used to adsorb the fusion. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native NT-4/5 may require modification to account for changes in the character of NT-4/5 or its variants upon expression in recombinant cell culture.

The trkB and trkC receptor DNA sequences are known. The receptors can be expressed to obtain a soluble form of the receptor by identifying the extracellular domain and excising the transmembrane domain therefrom). The soluble form of the receptor can then be used to screen for trkB or trkC binding molecules, preferably small organic molecules, that are candidate agonists for receptor activity. Screening of agonists uses, for example, transformed cells expressing trkB or trkC receptor. Further or alternative screening uses the assays taught herein.

As discussed above variants of native neurotrophins are made that act as agonists. The receptor binding site(s) of a neurotrophin are determined by binding studies. These regions can be subcloned and tested for agonist activity. Such regions can be also be constructed into larger molecules using known protein engineering techniques, such as template-assembly synthesis. Standard mutagenesis techniques (deletion or radical substitution of appropriate nucleic acids) are used to identify such regions and to create mutants for testing for agonism. Agonist activity can be determined by several means, including the assays described herein.

Chimeric or pantropic neurotrophins that bind either trkB or trkC or preferably both are suitable for use in the methods and compositions of the invention. By the term "pantropic neurotrophins" or "pantropic neurotrophic factors", or grammatical equivalents, herein is meant a neurotrophin which, unlike naturally occurring neurotrophins, has multiple neurotrophin specificities. That is, it contains domains which confer different neurotrophin specificities. WO 95/33829 and corresponding U.S. Ser. No. 08/253,937, are hereby incorporated by reference for describing, making and using pantropic neurotrophic factors suitable for practicing the present invention. The discussions herein pertaining to NT-4/5 or pantropic neurotrophin synthesis, design, expression and use apply to chimeric and other neurotrophins as well. In one embodiment, this means that the pantropic neurotrophins of the present invention will bind to a variety of neurotrophic receptors. Thus, for example, naturally occurring NGF, which is the natural or native ligand for the trkA receptor, does not bind appreciably to either the trkB or trkC receptor with high affinity; for example, NGF binds to these receptors with a 500–1000 fold lower $K_D$ than BDNF or NT-3, respectively. However, a pantropic NGF, i.e. a pantropic neurotrophin whose amino acid backbone is based on NGF, may bind to at least the trkA, trkB and p75 receptor. Alternatively, a pantropic NGF will bind to the trkA, trkC and p75 receptor. One preferred embodiment allows the binding of the trkA, trkB, trkC and p75 receptor. Similarly, naturally occurring BDNF and NT-4/5, which are the natural ligands for the trkB receptor, do not bind appreciably to either the trkA or trkC receptor as above. Thus pantropic BDNF or NT-4/5 will bind to trkB and any combination of trkA, trkC and p75, as shown above for pantropic NGF.

In alternative embodiments, the naturally occurring neurotrophin will bind with poor affinity to several neurotrophin receptors. In this embodiment, the pantropic neurotrophin binds to these receptors with affinities higher than normally found, similar to the affinities seen for the natural ligand. For example, NT-3 binds strongly to trkC, and weakly to trkA and trkB. Thus, a pantropic NT-3 binds to trkC with its normal binding affinity, and will bind to either trkA with an affinity similar to the trkA natural ligand, NGF, or to trkB with an affinity similar to the trkB natural ligands BDNF or NT-4/5, or both.

In a preferred embodiment, methods of treatment use a chimeric or pantropic neurotrophin or variant with a binding affinity for neurotrophin receptors at least about 50–60%, preferably about 75–80%, and even more preferably about 90%, and most preferably 100% of the binding affinity of the natural ligand. Thus, a pantropic NGF will bind to the trkB or trkC receptor with at least 50% of the binding of BDNF or NT-4/5, or NT-3, respectively. This affinity is measured by a variety of ways, as will appreciated by those skilled in the art. The preferred method is the use of competition assays, as shown in (Hulme, et al.) and in Example 2. Generally, binding affinities are reported as $IC_{50}$, that is, the concentration of unlabeled competitor which inhibits 50% of the binding of labeled ligand to the receptor.

In alternative embodiments, the pantropicity of the neurotrophin is measured not by binding affinity to neurotrophin receptors, but rather by the neuronal survival or neurite outgrowth assays. Thus, all neurotrophins support the survival of embryonic neural crest-derived sensory neurons. Survival of embryonic sympathetic neurons is only supported by NGF, while survival of placode-derived sensory neurons is supported by NT-3 and BDNF (Grotz et al., 1992). Survival of sensory neurons of the dorsal root ganglion is supported by both NGF and BDNF. NT-3 elicits neurite outgrowth of sensory neurons from dorsal root ganglion, sympathetic chain ganglia, and nodose ganglion, as well as supports survival of nodose ganglia neurons and dorsal root ganglion neurons. Thus, neuronal survival assays or neurite outgrowth assays can be run to determine the pantropicity of the pantropic neurotrophins.

Thus, neurotrophin specificity is determined by the neurotrophin receptor binding, and the neuronal survival assays and/or neurite outgrowth assays. Thus, a pantropic neurotrophin with NGF specificity means a neurotrophin which exhibits at least the binding characteristics, neuronal survival assay specificity, or the neurite outgrowth assay specificity of NGF. Similarly, a pantropic neurotrophin with BDNF, NT-3 or NT-4/5 specificity exhibits at least the binding characteristics, neuron survival assay specificity, or neurite outgrowth assay specificity of BDNF, NT-3 or NT-4/5, respectively.

In an additional embodiment, pantropic neurotrophins are made by constructing covalent heterodimers. Normally, neurotrophins are homodimers, comprising two identical monomers which are non-covalently associated. In this embodiment, as outlined below, pantropicity is conferred by each monomer containing domains which confer different neurotrophic specificity. Alternatively, pantropicity may be created by covalently attaching two different neurotrophins with different specificities to create a covalent heterodimer. Thus, for example, a NGF monomer may be covalently attached to a NT-3 monomer, resulting in a pantropic neurotrophin with both NGF and NT-3 specificity. Similarly, covalent heterodimers may be made with any combination of NGF, NT-3, NT-4/5, BDNF or CNTF to create pantropic neurotrophins with at least two specificities. In addition, this procedure may be done with monomers which are themselves pantropic, resulting in covalent dimers of any combination of pantropic and single specificity monomers. Thus, a pantropic covalent dimer may be a homodimer of two pantropic monomers. However, to be included within the definition of the present invention, the pantropic covalent dimer must have at least two, and preferably three, neurotrophin specificities.

The covalent attachment is preferably done as a direct fusion of the nucleic acid, such that when the protein is expressed, the C-terminus of the first monomer is attached directly to the N-terminus of the second monomer, creating a single nucleic acid encoding dimer. In alternative embodiments, a linker may be used, such as short repeats of glycine, or glycine and serine; for example, a linker such as gly-gly or gly-gly-ser-gly-gly (SEQ ID NO: 28) may be used. This is done using techniques well known in the art. Other techniques for the covalent attachment of proteins are well know in the art.

Pantropic neurotrophins accomplish pantropic binding, or, as discussed above, pantropic neuronal survival, by containing domains which confer neurotrophin receptor specificity or binding. A domain may be defined in one of two ways. In the first embodiment, a domain is a portion of the neurotrophin which confers some neurotrophic specificity. In this embodiment, a single monomer of the pantropic neurotrophin contains one or several domains which confer different specificities. The domains can range in size from a single amino acid to about 10–15 amino acids. The domain may be comprised of a combination of amino acids from a different neurotrophin than the host neurotrophin, i.e. a domain from one neurotrophin may be substituted into a second neurotrophin, conferring pantropicity to the second neurotrophin. Alternatively, the domain may result from amino acid substitutions which are not based on homology to existing neurotrophins, as outlined below. In the preferred embodiment, the domain comprises a continuous sequence of amino acids; that is, a single stretch of amino acids is replaced. In other embodiments, the domain may be comprised of discontinuous amino acids; for example, several regions within the neurotrophin may confer specificity, and thus replacements at several positions within the neurotrophin are necessary for pantropicity.

In some embodiments, there is more than one domain within a neurotrophin which can confer neurotrophic specificity, which will depend on the particular neurotrophin. BDNF, for example, has a number of domains which appear to confer BDNF specificity. The present invention shows that single amino acid change in NT-3 (SEQ ID NO: 2), from aspartic acid at position 15 to alanine, confers BDNF specificity to NT-3. This domain can also be imported into the NGF and NT-4/5 sequences at the positions that correspond to position 15 in NT-3; i.e. position 16 in NGF or position 18 in NT-4/5. It should be understood that the corresponding amino acids are determined by an examination of the alignment of the sequences as depicted in U.S. Pat. No. 5,364,769. In addition to this domain, there are other domains within BDNF which confer BDNF specificity. For example, the substitution of the BDNF sequence (SEQ ID NO: 3) from positions 78 to 88 (QCRTTQSYVR) (SEQ ID NO: 29), or from positions 93–99 (SKKRIG) (SEQ ID NO: 30) may confer BDNF specificity (55).

Similarly, NT-3 has a number of domains which may confer NT-3 specificity when substituted into a different neurotrophin. A number of residues of NT-3 have been shown to be important in NT-3 trkC receptor binding as well as bioactivity assays. Specifically, mutations at positions R103, D105, K80, Q83, E54, R56, T22, Y51, V97, Y11, E7, R8, E10 and R68 all contribute to NT-3 specificity, since mutations at these positions in NT-3 cause decreases in NT-3 activity. Of these, K80, Q83, T22, and V97 are within variable regions, and the rest are found within constant regions. In addition, residues in the vicinity of the residues may also give NT-3 specificity. In some embodiments, changes in the constant regions may also give NT-3 specificity. Alternatively, mutations at positions R31 and E92 caused increases in NT-3 binding; specifically, R31A and E92A NT-3 showed increased trkC binding. These mutations can be directly imported into neurotrophins besides NT-3, using the procedures described below. The amino acids at any of these positions may be changed, as outlined below.

NGF (SEQ ID NO: 31) has a number of domains which may confer NGF specificity when substituted into a different neurotrophin. The N-terminal amino acids of NGF confer NGF specificity when substituted for the N-terminal residues of NT-3. Specifically, the 7 N-terminal amino acids (SSSHPIF) (SEQ ID NO: 32) of NGF may be substituted for the 6 N-terminal amino acids of NT-3 (YAEHKS) (SEQ ID NO: 14), resulting in a pantropic NT-3 with NGF specificity. The exact number of NGF N-terminal residues is not crucial; as shown in the Examples, and particularly in Example 3, the histidine at amino acid position 4 appears to be quite important for NGF specificity; thus from about 4 to about 10 N-terminal residues may be exchanged although in some embodiments, a single amino acid change will be sufficient. Similarly, a number of other residues of NGF have been shown to be important in NGF trkA receptor binding as well as bioactivity assay. For example, there are a number of residues which, when mutated, lose NGF activity. This shows the importance of the residue for NGF specificity. These residues include, but are not limited to H4, P5, V18, V20, G23, D30, Y52, R59, R69, H75, Y79, T81, and R103. Of these, D30, R59, Y79, and T81 are in "variable regions," i.e., regions which vary between the different neurotrophins, with the remainder in constant regions. In some embodiments, the variable region residues are more likely to cause NGF specificity, since constant region residues may be important for general structure and characteristics, and may not confer specificity. However, as shown above for the D15A mutation, mutations in the constant regions can confer specificity as well. Furthermore, there are a number of amino acid substitutions in NGF which increase NGF binding and/or bioactivity. Accordingly, these substitutions may be imported into other neurotrophin backbones to confer NGF specificity. These residues include, but are not limited to E11, F12, D24, E41, N46, S47, K57, D72, N77, H84, D105, and K115.

Once identified, the residues important in neurotrophin specificity can be replaced by any of the other amino acid residues using techniques described in the examples and well-known techniques for site-directed mutagenesis. Generally, the amino acids to be substituted are chosen on the basis of characteristics understood by those skilled in the art. For example, when small alterations in the characteristics are desired, substitutions are generally made as discussed above.

In the context of a covalent heterodimer, a domain may also refer to the entire neurotrophin monomer. Thus, a pantropic covalent heterodimer can be comprised of a domain which confers NT-3 specificity, i.e. the NT-3 monomer, covalently attached to a domain that confers BDNF specificity, i.e. the BDNF monomer. Similarly, an NT-3 monomer may be paired with an NGF monomer, or an NGF monomer may be paired with a BDNF monomer. In addition, covalent heterodimers may be made with NT-4/5 and CNTF monomers as well. In these embodiments, the domain is large, and generally comprises most or all of the wild-type neurotrophin amino acid sequence.

In one embodiment, the agonist is a pantropic or chimeric NT-3. In this context, a pantropic NT-3 is a pantropic neurotrophin which has an amino acid sequence homologous to the amino acid sequence of NT-3, with domains which confer other neurotrophin specificities. In the preferred embodiment, the domains are substituted for NT-3 residues; that is, some number of amino acids are deleted from the NT-3 sequence, and an identical or similar number of amino acids are substituted, conferring an additional specificity. For example, the MNTS-1 (multiple neurotrophic specificities-1) pantropic NT-3 comprises the first 7 amino acids of NGF replacing the 6 N-terminal residues of NT-3, plus the D15A substitution. The MNTS-1 pantropic NT-3 has NT-3, NGF, and BDNF specificities, and also binds to the p75 receptor. Other pantropic NT-3s are made using minimal changes within the N-terminus. For example, since H4 and P5 are conserved among NGFs, and 2 hydrophobic residues in positions 6 and 7 are conserved, the following variants are made: 1) YASHPIF-hNT-3 (SEQ ID NO: 33); 2) YAI-IPIF-hNT-3 (SEQ ID NO: 34); 3) YASHPIS-hNT-3 (SEQ ID NO: 35); (4) YAEHPIF-hNT-3 (SEQ ID NO: 36); 5) YAQHPIF-hNT-3 (SEQ ID NO: 37). When the D15A substitution is added, the resulting neurotrophins exhibit NGF, NT-3 and BDNF specificity. Alternatively, replacing the variable region 2 or 3 or 4 or combinations, of NT-3 with the corresponding region from NGF gives a pantropic neurotrophin with both NT-3 and NGF specificity. A pantropic NGF can be made with a D16A substitution, which confers BDNF specificity, plus substitutions in the pre-variable region 1 (V18E+V20L+G23T) and in variable region 4 (Y79Q+T81K+H84Q+F86Y+K88R). Alternatively, the substitutions in the pre-variable region 1 can be made with only single amino acid substitution in variable region 4; for example, V18E+V20L+G23T and one of Y79Q, T81K, H84Q, F86Y, or K88R may be made.

In a preferred embodiment, the agonist is a chimeric or pantropic NT-4/5, preferably made with a trkC binding region. NGF specificity may be conferred on NT-4/5 by replacing the N-terminal 9 amino acids of NT-4/5 with the N-terminal 7 amino acids of NGF.

In one embodiment, binding to the p75 receptor by the pantropic neurotrophin has been substantially diminished or eliminated. For example, there are a variety of amino acid residues which contribute to p75 binding, in which mutations result in diminished p75 binding. In NT-3, mutations at positions R68, Y11, K73, R114, K115, Y51, K73, R31 and H33 and in NGF, mutations at positions F12, I31, K32, K34, K50, Y52, R69, K74, K88, L112, S113, R114, and K115 all result in diminished p75 binding. Since F12, I31, K50, Y52, R69, and K74 are all within constant regions of the neurotrophins; these changes are expected to alter p75 binding in the other neurotrophins as well. The other residues may be altered as well.

In addition to the amino acid changes outlined above, those skilled in the art understand that some variability of the amino acid sequence is tolerated without altering the specificity and characteristics of the neurotrophin. Thus, pantropic neurotrophins can have amino acid substitutions, insertions or deletions compared to the wild-type sequences which do not affect pantropicity but are merely variations of the sequence. In some embodiments, these mutations will be found within the same positions identified as important to specificity; i.e. in some cases, neutral mutations may be made without changing neurotrophin specificity.

The pantropic neurotrophins of the present invention can be made in a variety of ways, using recombinant technology as discussed above. In a preferred embodiment, the pantropic neurotrophins of the invention are expressed in mammalian cells. Mammalian expression systems are also known in the art. In one embodiment, pantropic neurotrophins are produced in yeast cells. Yeast expression systems are well known in the art, and include expression vectors for *Saccharomyces cerevisiae, Candida albicans* and *C. maltosa, Hansenula polymorpha, Kluyverornyces fragilis* and *K. lactis, Pichia guillerimondii* and *P. pastoris, Schizosaccharomyces pombe,* and *Yarrowia lipolytica.* The methods of introducing exogenous nucleic acid into yeast hosts, as well as other hosts, is well known in the art, and will vary with the host cell used. In a preferred embodiment, pantropic neurotrophins are expressed in bacterial systems. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others. In one embodiment, pantropic neurotrophins are produced in insect cells. Expression vectors for the transformation of insect cells, and in particular, baculovirus-based expression vectors, are well known in the art. Materials and methods for baculovirus/insect cell expression systems are commercially available in kit form; for example the "MaxBac" kit from Invitrogen in San Diego. Recombinant baculovirus expression vectors have been developed for infection into several insect cells. For example, recombinant baculoviruses have been developed for *Aedes aegypti, Autographa californica, Bombyx mori, Drosophila melangaster, Spodoptera frugiperda,* and *Trichoplusia ni.*

Once expressed, chimeric or pantropic neurotrophins are used as neurotrophic factors. These chimeric or pantropic neurotrophins may be utilized in various compositions, assays, and therapeutic applications of the invention For use in the assays of the invention the agonist can be labeled. By "labeled" herein is meant an agonist that has at least one element, isotope or chemical compound attached to enable the detection of the neurotrophin bound to a neurotrophin receptor. In general, labels fall into three classes: a) isotopic labels, which may be radioactive or heavy isotopes; b) immune labels, which may be antibodies or antigens; and c) colored or fluorescent dyes. The labels may be incorporated into the neurotrophin at any position. Once labelled, the neurotrophins are used to detect neurotrophin receptors, either in vitro or in vivo. For example, the presence of neurotrophin receptors can be an indication of the presence of certain cell types, useful establishing and in scoring the assays. That is, a subpopulation of certain cell types may be shown by the binding of the labeled neurotrophin to the cells via the receptors.

Additionally, the neurotrophins are useful as standards in assays of the invention. For example, the activity of a variant neurotrophin in any particular assay may be determined using known neurotrophin standards, and then the variant neurotrophin may be used in the diagnosis and quantification of neurotrophins and other agonists.

As will be understood by those skilled in the art, the pantropic neurotrophins of the present invention can replace other neurotrophic factors which are used as media components in the cultures as taught herein and in teh methods of treatment taught herein. The amount of the pantropic neurotrophins to be added can be easily determined using standard assays.

Purification of Agonists

Techniques used for separating the agonist from impurities depend on which particular agonist is being employed.

These procedures may include, for example, one or more steps selected from immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the trkB or trkC agonist, such as trkB or trkC receptors or antibody-affinity, and ethanol or ammonium sulfate precipitation. A protease inhibitor may be included in any of the foregoing steps to inhibit proteolysis. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

Therapeutic Compositions and Administration of Agonists

Agonists to trkB or trkC alone, in combination with each other, or optionally in combination with ototoxic pharmaceuticals, are believed to find use as drugs for in vivo treatment of mammals, ex vivo treatments involving transplant or assays involving organs such as during perfusion, and in vitro assays and screening methods. For example, the trkB or trkC agonist alone or in combination with each other will be useful in treating balance impairments in cases where pharmaceutical drugs are limited in their dosage or display side-effect of a oto-neurological balance impairment.

In the preferred embodiment, the neurotrophin(s) is administered to a patient to treat neural-related (associated with neuron degeneration, damage or loss) imbalance impairment, prophylactically or therapeutically. Preferably hair cell loss or damage is not present or not at a significant level that would hinder balance recovery. Specific examples include, but are not limited to neuropathies, and other conditions characterized by necrosis, damage, or loss of neurons affecting balance, whether caused by trauma, injury, aging, noise, environmental toxins, or ototoxic pharmaceutical drugs. For example, neuropathies associated with certain conditions such as diabetes, AIDS, or chemotherapy may be treated using the compositions and methods of the present invention.

Therapeutic formulations of agonist(s) (and optionally ototoxic pharmaceutical drug) for treating balance impairments are prepared for storage by mixing the agonist(s) or drug having the desired degree of purity with optional physiologically acceptable carriers, excipients, or stabilizers (Remington's Pharmaceutical Sciences, 16th edition, Oslo, A., Ed., [1980]), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins-chelating agents such as EDTA; sugar alcohols such as mannitol or sorbitol; salt-forming counterions such as sodium; and/or nonionic surfactants such as Tween, Pluronics, or polyethylene glycol (PEG).

The agonist(s) are also suitably linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The agonist(s) to be used for in vivo administration must be sterile. This is readily accomplished by filtration through sterile filtration membranes, prior to or following lyophilization and reconstitution. The agonist(s) ordinarily will be stored in lyophilized form or in solution. Preferably, it is free or substantially free (at least 80%, preferably at least 90%, more preferably at least 95%, and even more preferably at least 99% pure) of contaminating polypeptides from the purification source.

Therapeutic agonist compositions generally are placed into a container having a sterile access port, for example, an intravenous solution bag or vial having a stopper pierceable by a hypodermic injection needle.

The agonist(s) is administered in an acute or chronic fashion, as may be required, for prophylactic and therapeutic applications, by a number of routes including: injection or infusion by intravenous, intraperitoneal, intracerebral, intramuscular, intradermally, intraocular, intraarterial, subcutaneously, or intralesional routes, topical administration, orally if an orally active small molecule is employed, using sustained-release systems as noted below, or by an indwelling catheter using a continuous administration means such as a pump, by patch, or implant systems, e.g., intracerebral implantation of a sustained-release vehicle. Agonist(s) is administered continuously by infusion or by periodic bolus injection if the clearance rate is sufficiently slow, or by administration into the blood stream, lymph, CNS or spinal fluid. A preferred administration mode is directly to the affected portion of the ear or vestibule, topically, and, preferably to the affected neurons, so as to direct the molecule to the source and minimize side effects of the agonists.

Neurotrophin, preferably NT-4/5, can be injected through chronically implanted cannulas or chronically infused with the help of osmotic minipumps. Subcutaneous pumps are available that deliver proteins through a small tubing to the appropriate area. Highly sophisticated pumps can be refilled through the skin and their delivery rate can be set without surgical intervention. Examples of suitable administration protocols and delivery systems involving a subcutaneous pump device or continuous infusion through a totally implanted drug delivery system are those used for the administration of dopamine, dopamine agonists, and cholinergic agonists to Alzheimer patients and animal models for Parkinson's disease described by Harbaugh, J. Neural Transm. Suppl., 24: 271–277 (1987) and DeYebenes et al., Mov. Disord., 2: 143–158 (1987), the disclosures of which are incorporated herein by reference. It is envisioned that it may be possible to introduce cells actively producing agonist into areas in need of increased concentrations of agonist.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15: 167–277 [1981] and Langer, Chem. Tech., 12: 98–105 [1982] or poly (vinylalcohol)), polylactides (U.S. Pat. No. 3,773,919, EP 58,481), copolymers of L-glutamic acid and gamma ethyl-L-glutamate (Sidman et al., Biopolymers, 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133, 988). The agonist(s) also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Osol, A., Ed., (1980).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release agonist(s) compositions also include liposomally entrapped agonist(s). Liposomes containing agonist(s) are prepared by methods known per se: DE 3,218,121; Epstein et al., Proc. Natl. Acad. Sci. USA, 82: 3688–3692 (1985); Hwang et al., Proc. Natl. Acad. Sci. USA, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal agonist therapy. A specific example of a suitable sustained-release formulation is in EP 647,449.

An effective amount of agonist(s) to be employed therapeutically will depend, for example, upon the therapeutic objectives, the route of administration, the species of the patient, and the condition of the patient. Accordingly, it will be necessary for the therapist to titer the dosage and modify the route of administration as required to obtain the optimal therapeutic effect. As is known in the art, adjustments for age as well as the body weight, general health, sex, diet, time of administration, drug interaction and the severity of the disease may be necessary, and will be ascertainable with routine experimentation by those skilled in the art. A typical daily dosage of TrkB or trkC agonist used alone might range from about 1 µg/kg to up to 100 mg/kg of patient body weight or more per day, depending on the factors mentioned above, preferably about 10 µg/kg/day to 10 mg/kg/day. Typically, the clinician will administer agonist until a dosage is reached that repairs, maintains, and, optimally, reestablishes neuron function to relieve the imbalance impairment. Generally, the agonist is formulated and delivered to the target site at a dosage capable of establishing at the site an agonist level greater than about 0.1 ng/ml, more typically from about 0.1 ng/ml to 5 mg/ml, preferably from about 1 to 2000 ng/ml. In a specific embodiment of the invention, a pharmaceutical composition effective in promoting the survival of VGNs may provide a local neurotrophin protein concentration of between about 1 and 100 ng/ml, preferably 5 to 25 ng/ml, and more preferably, between 10 and 20 ng/ml. The progress of this therapy is easily monitored by conventional assays and neurological diagnostic methods.

If two agonists are administered together, they need not be administered by the same route, nor in the same formulation. However, they can be combined into one formulation as desired. In a preferred embodiment NT-4/5 optionally is combined with or administered in concert with or formed as a pantropic neurotrophin with a neurotrophic agonist to trkC. Both agonists can be administered to the patient, each in effective amounts, or each in amounts that are sub-optimal but when combined are effective. Preferably such amounts are about 10 µg/kg/day to 10 mg/kg/day of each. In another preferred embodiment, the administration of both agonists is by injection using, e.g., intravenous or subcutaneous means, depending on the type of agonist employed. Typically, the clinician will administer the agonist(s) until a dosage is reached that achieves the desired effect for treatment of the balance impairment. The progress of this therapy is easily monitored by conventional assays.

The two types of agonists, if used together, may be formulated together in an appropriate carrier vehicle to form a pharmaceutical composition that preferably does not contain cells. In one embodiment, the buffer used for formulation will depend on whether the composition will be employed immediately upon mixing or stored for later use, since long-term storage may bring into issue stability such as solubility and aggregation that can be addressed by altering the pH. The final preparation may be a stable liquid or lyophilized solid.

The agonist(s) optionally is combined with or administered in concert with ototoxic pharmaceutical drugs. Initially the drugs are administered in conventional therapies known for the ototoxic pharmaceutical. Adjustments to the therapies are at the discretion of the skilled therapist to titrate dosages and conditions that decrease ototoxicity-related imbalance while maintaining, and preferably improving, treatment outcomes with the ototoxic pharmaceutical drug.

Accordingly, methods for preventing or reducing ototoxicity of an aminoglycoside antibiotic or other ototoxic pharmaceutical are disclosed herein, which comprise the administration of an effective dose of a trkB or trkC agonist. In addition, provided herein are compositions having reduced ototoxicity as a result of incorporation of the ototoxicity-inhibiting trkB or trkC agonists of the present invention. These pharmaceutical compositions comprise an effective ototoxicity-inhibiting amounts of agonists as described herein, therapeutically effective amounts of the ototoxic pharmaceutical drug, e.g. aminoglycosides antibiotic, anti-neoplastic agent such as cisplatin, and optionally a pharmaceutically acceptable carrier and/or vehicle which would be familiar to one skilled in the pharmaceutical arts. The actual amounts of ototoxic pharmaceutical drug employed will range from those given in standard references for prescription drugs, e.g. "Physicians Desk Reference" (1995), "Drug Evaluations" AMA, 6th Edition (1986); to amounts somewhat larger since the ototoxicity potential is reduced in these compositions.

The effective amounts of such agents, if employed, will be at the physician's or veterinarian's discretion. Dosage administration and adjustment is done to achieve the best management of imbalance (and when used in conjunction with an ototoxic pharmaceutical drug, the indication for the ototoxic drug). The dose will additionally depend on such factors as the type of drug used and the specific patient being treated. Typically the amount employed will be the same dose as that used if the drug were to be administered without agonist; however, lower doses may be employed depending on such factors as the presence of side-effects, the condition being treated, the type of patient, and the type of agonist and drug, provided the total amount of agents provides an effective dose for the condition being treated. For example, a test dose may be 5 mg, which is then ramped up to 10–20 mg per day, once a day, to 25 mg twice per day (BID) or three times per day (TID), and may be titrated to 50 mg BID or TID as the patient tolerates it. Tolerance level is estimated by determining whether decrease in imbalance impairment is accompanied by signs of observed side-effects. A discussion of the dosage, administration, indications and contraindications associated with ototoxic pharmaceuticals optionally used with the neurotrophins in the methods of the invention can be found in the *Physicians Desk Reference*, Medical Economics Data Production Co., Montvale, N.J. (1995).

In preferred embodiments therapeutic formulations contain NT-4/5, a fragment, variant, or pantropic, and can be prepared for storage by mixing NT-4/5 having the desired degree of purity with optional physiologically acceptable carriers, excipients or stabilizers (Remington's Pharmaceutical Sciences, supra,) in the form of lyophilized cake or aqueous solutions.

The compositions herein also may suitably contain other peptide growth factors, most preferably hair cell growth factors, perhaps retinoic acid. Such growth factors are suitably present in an amount that is effective for the purpose intended, i.e., to promote restoration or recovery of hair cells when desired, or to enhance growth or recovery of neurons. Although the present results indicate that particular neurotrophins have strong protective effects on VGNs, they did not protect hair cells from the ototoxic drugs. If hair cell loss due to ototoxicity is significant, balance impairment recovery could be improved by new hair cell growth or regeneration. Recent studies have suggested possible candidates (Forge et al., 1993; Cotanche and Lee, 1994; Tsue et al., 1994a; Cotanche and Lee, 1994; Kelley et al., 1995). For example, diffusible factors such as TGF-α and EGF (Lambert, 1994; Yamashita and Oesterle, 1995) or components derived from antibiotic treated inner ear tissue (Tsue et al., 1994b) stimulate proliferation of supporting cells. Retinoic acid alone or in combination with TGF-α facilitates hair cell regeneration in vitro (Lefebvre et al., 1993, 1995). As taught herein, neurotrophins will provide for prevention of neuronal cell death after injury or insult by ototoxins.

The effectiveness of treating balance impairments with the methods of the invention can be evaluated by the following signs of recovery, including recovery of normal balance function, which can be assessed by known diagnostic techniques including those discussed herein, and normalization of nerve conduction velocity, which is assessed electrophysiologically.

In another embodiment, agonist compositions of the invention are used during clinical utricle implants to keep or improve viability of vestibular ganglion neurons. Preferably a combination of a trkB and a trkC neurotrophin and a hair cell growth factor(s) will be used, either alone or in combination with a utricle implant.

Utricle Explants

In one embodiment of the invention is provided a method of assaying for a trkB or trkC agonist that provides vestibular ganglion neuron protection or survival from an ototoxin. The assay steps include culturing a utricle explant, administering a trkB or trkC agonist to the culture, administering an ototoxin to the culture, and determining the amount of protection or survival compared to a control culture to which the trkB or trkC agonist was not administered.

In a preferred embodiment of the invention is provided an organotype utricle explant culture that utilizes a 3-D collagen matrix cultures and maintains its normal, in vivo architecture to provide a vestibular assay system. The vestibular ganglion remain attached. The explant is cultured in three-dimensional ("3-D") collagen gel in serum free medium.

Embedding the utricle explants in the 3-D collagen was better for maintaining their normal architecture than floating the explants or placing the explants on a monolayer substrate, since the explant tissue could be kept unfolded and cell migration out of the tissue could be limited. By using neurofilament (N52) and phalloidin-FITC conjugate double labeling, the integrity of VGNs and the hair cells in the utricle was demonstrated. Utricle explants prepared according to the invention maintained normal architecture in the 3-D collagen gel cultures as observed by Nomarski micrographs of utricle tissue dissected from P3 rats and grown for 2 days in vitro at low and high magnifications. The VGNs and hair cells in the explants grew well and maintained their normal connectivity. The VGNs and hair cells remained in their normal locations. No gross cell death of VGNs and hair cells occurred under this culture condition. Organotypic cultures of postnatal utricle explants provided herein, in which the innervation of hair cells by vestibular neurons are intact, are useful to examine ototoxicity of different classes of ototoxins, including ototoxic pharmaceutical drugs, for example, salicylate, gentamicin, and cisplatin, and to search for or test candidate agents that protect against the ototoxic effect. To determine if an ototoxin is able to induce degeneration of VGNs and/or hair cells in the utricle explant cultures, the ototoxin is added at different concentrations to the culture after allowing the culture to recover from the in vitro explant. Cell count of remaining hair cells and VGNs can be done to determine and quantify ototoxic effect. Since the density of the axons of VGNs is a reliable index of the number of surviving VGNs, in one embodiment the number of the VGN axons from a given length (100 $\mu$m) in the middle of the utricle is counted. Phalloidin-labeled hair cells were also counted in the same way.

Organotypic culture of utricle explants offers advantages to explore the mechanism of actions of ototoxins, to discover protective agents, and to search for hair cell growth factors, as it keeps the afferent neuronal innervation of hair cells intact and appears to follow closely the normal development pathway. According to the present invention, provided herein is a reliable, rapid, and facile method of testing the effects of ototoxic agents and the drugs that prevent, reduce or treat these ototoxic effects. As exemplified herein an organotypic culturing of postnatal cochlear explants in a 3-D collagen matrix in well defined, serum-free medium provides these advantages without the need for a cumbersome Maximov slide assembly (Sobkowicz et al., 1975; Rastel et al., 1993) or undefined medium. Embedding the utricle explants in the 3-D collagen was better for maintaining the normal architecture than floating the explants or placing the explants on a monolayer substrate, since the explant tissue could be kept unfolded and cell migration out of the tissue could be limited.

The following examples serve to more fully describe the manner of using the above-described invention. The following examples are offered by way of illustration and not by way of limitation. The disclosures of all citations in the specification are expressly incorporated herein by reference.

EXAMPLES

Example I

NT-4/5, BDNF and NT-3, but not NGF, Enhance VGN Survival in Culture

The effects of trkB or trkC agonists to enhance neuronal survival was determined using VGNs in cell culture. VGN cell culture was prepared as follows. Vestibular ganglia were dissected from postnatal day 5 (P5) Wistar rats and were incubated in a mixture of 0.125% trypsin and 0.125% collagenase for 25 min at 37° C. The enzyme was inactivated with a mixture of 0.005% soybean trypsin inhibitor (Sigma) and 0.005% DNase (Worthington) before trituration with 0.05% DNase in Eagle's Basal Medium ("BME"). After the undissociated tissues were separated by filtering with a Nylon meshwork (33 μm in pore size), the dissociated cells were preplated on a 35 mm untreated tissue culture dish for 25 min to enrich the neuronal population. Under these experimental procedures, about 3–5% of the cell population were vestibular ganglion neurons (VGNs) as determined by immunocytochemistry with a monoclonal antibody (N52; Boehringer) against neurofilament (200 kd). The cell suspension was finally plated on polylysine (500 μg/ml)laminin (20 μg/ml) coated 16-well LabTek slides in 200 μl of serum-free medium (BME plus serum-free supplement (Sigma I-1884), 1% BSA, 2 mM glutamine, and 5 mg/ml glucose) containing no antibiotics. Cells were plated at a density of 100,000/well.

All human recombinant neurotrophins (obtained from Genentech, Inc.) were added to the cultures at the time of plating.

Cell counts and data analysis were performed as follows. After 2 days in culture, viable VGNs were identified by labeling with the neurofilament monoclonal antibody N52 and counted using a grid ocular reticule covering an area of 1 mm$^2$ under a Zeiss Axiophot microscope. For each culture, about 10 randomly selected fields were counted. In these experiments, cell counts were performed in the same way for control cultures. Data were collected from triplet cultures for each of the experimental groups. Data were then normalized as a percentage of the viable VGNs in the control cultures in each of the experiments.

Immunohistochemistry and immunocytochemistry were performed as follows. For double antibody labeling, vestibular ganglia were dissected from P5 rats and immersed immediately in 4% paraformaldehyde (in 0.1M phosphate buffer, pH 7.4) for 1 hr. After the vestibular ganglia were cryoprotected with a 30% sucrose solution, cross sections were cut on a cryostat. The sections were first blocked with a 10% normal goat serum in 1% triton-X 100 in phosphate buffered saline (PBS) for 20 min and then incubated with a mixture of the monoclonal antibody N52 against neurofilament 200 kD (5 μg/ml) and a rabbit antibody against the extracellular domain of trkB (anti-trkB$_{23-36}$, 2 μg/ml; Yan et al., 1994; Gao et al., 1995), a trkA antiserum (1:10,000, Clary et al., 1994), or an antiserum against p75 (1:10,000, Weskamp and Reichardt; 1991) in PBS containing 3% normal goat serum and 1% Triton-X 100 overnight at 4° C. FITC-conjugated goat anti-mouse and Texas red-conjugated goat anti-rabbit secondary antibodies (1:70–100; Cappel) were then used to reveal the double labeling pattern on the sections of vestibular ganglion. For horse radish peroxidase-mediated neurofilament immunostainings, VGN cultures were fixed in 4% paraformaldehyde (in 0.1M phosphate buffer, pH 7.4) for 30 min, washed in PBS (pH 7.4), and the immunostainings were performed using a biotinylated sheep anti-mouse secondary antibody and a streptavidin-horse radish peroxidase conjugate (1:200, Amersham Life Science), as described elsewhere.

Figure 1:
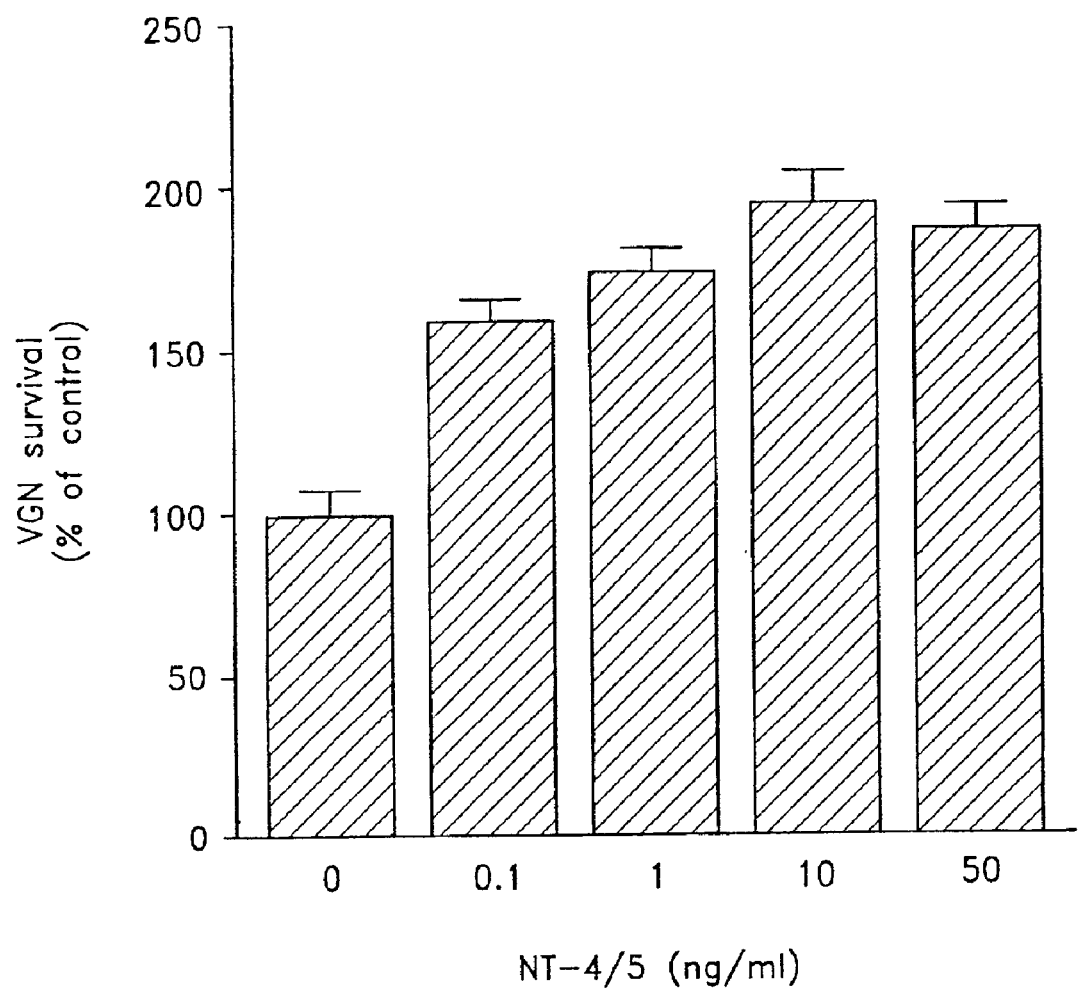
FIG. 1 is a histogram depicting the effects of NT-4/5 on VGN survival. VGNs were prepared from P5 rats, plated and cultured for 2 days in serum-free medium in the absence or presence of NT-4/5 at different concentrations. Viable VGNs were identified by neurofilament monoclonal antibody (N52) labeling under a Zeiss Axiophoto microscope and counted using a grid ocular reticule covering an area of 1 $mm^2$. For each culture, about 10 randomly selected fields were counted. Data were collected from triplet cultures, and normalized as a percentage of the number of viable neurons in the control cultures in each of the experiments. The error bars indicate SEM. As compared to control cultures, NT-4/5 displayed very significant survival-promoting effects on VGNs at all doses tested ($p<0.01$, 2-tailed, unpaired t-test).

The effect of neurotrophins on cell survival was determined on VGNs which were dissociated from postnatal day 5 (P5) rat vestibular ganglia and plated in defined serum-free medium. Neurofilament protein immunocytochemistry using bright field microscopy was performed in the VGN cultures in serum-free medium in the absence or presence of 10 ng/ml of NT-4/5. In control cultures in serum-free medium without neurotrophins, about 35% of VGNs survived after 2 days. When NT-4/5 was added to the culture, an up to 2-fold increase was seen in the number of neurons that survived, as identified by immunocytochemistry with a monoclonal antibody (N52) against neurofilament protein (200 kd), which labeled intensely both somata and processes of VGNs in the culture as well as in the vestibular ganglion (see below, FIG. 3). The survival-promoting effects of NT-4/5 on cultured VGNs were dose-dependent (FIG. 1). When different doses of NT-4/5 ranging from 0.1 to 50 ng/ml were examined, a maximal effect was seen at a concentration of 10 ng/ml.

Effects of other neurotrophins including NGF, BDNF, and NT-3, were also examined and compared to that of NT-4/5 on cultured VGNs at a concentration of 10 ng/ml (FIG. 2). BDNF was equivalent to NT-4/5 in promoting survival of VGNs ($p<0.001$ for both NT-4/5 and BDNF, as compared to control). NT-3 displayed a significant effect ($p<0.01$) but was less potent than NT-4/5 and BDNF ($p<0.05$). In contrast, NGF did not show any detectable effect in VGN cultures. To determine whether there were additive effects of the neurotrophins on VGN survival, NT-4/5 was combined with BDNF or NT-3 at a dose of 10 ng/ml; however, no synergistic effects were observed (FIG. 2).

When other growth factors including epidermal growth factor (EGF), basic fibroblast growth factor (βFGF), and insulin-like growth factor-1 (IGF-1) were added to the cultures at the time of plating at a concentration of 10 ng/ml, the number of surviving VGNs was not affected (FIG. 2), suggesting a selective response of VGNs to the three neurotrophins, NT-4/5, BDNF and NT-3.

Example II

TrkB-IgG and trkC-IgG Abolish Specifically the Survival-Promoting Effects of NT-4/5, BDNF and NT-3

TrkB-IgG and trkC-IgG have been previously reported to be specific antagonists for NT-4/5 (or BDNF) and NT-3, respectively (Shelton et al., 1995). To confirm that the survival-promoting effects of NT-4/5, BDNF and NT-3 were specific, trkB-IgG or trkC-IgG fusion protein was added to the culture along with NT-4/5, BDNF or NT-3. All human recombinant neurotrophins (Genentech, Inc.) were added to the cultures at the time of plating. To block the effects of the neurotrophins, 1 μg/ml of trkB-IgG or trkC-IgG (kindly provided by Dr. Dave Shelton), specific antagonists for NT-4/5 (and BDNF) or NT-3, respectively (Shelton et al., 1995), was added to some of the experimental cultures at the same time when neurotrophins were added.

As shown in FIG. 3, the presence of the trkB-IgG fusion protein completely abolished the survival-promoting effects of NT-4/5 or BDNF, but not that of NT-3. Similarly, addition of trkC-IgG inhibited the activity of NT-3 but not that of NT-4/5 or BDNF (FIG. 3). While trkB-IgG and trkC-IgG together blocked the effects of NNT-4/55 and NT-3, by themselves they did not show detectable effects in the VGN cultures. These results confirm the specificity of trkB-IgG or trkC-IgG and support the idea that the survival-promoting effects observed with trkB or trkC agonists NT-4/5, BDNF or NT-3 are specific.

Example III

VGNs Make trkB and p75 Proteins, but not trkA Protein

To determine which neurotrophin receptors are expressed by VGNs, immunohistochemistry with antisera against trkB (Yan et al., 1994; Gao et al., 1995), trkA (Clary et al., 1994) and p75 (Westkamp and Reichardt, 1991) was performed. Dual immunohistochemistry on cross sections of the vestibular ganglion with trkB, trkA, or p75 and neurofilament protein antibodies was performed. Texas red microscopy was used to show the staining pattern of antibodies against trkB, trkA and p75, respectively, while fluorescent microscopy was used to show the immunostainings of neurofilament antibody (N52) in the same sections. N52 clearly stained somata and processes of VGNs. Note that while VGN somata and processes were heavily labeled by trkB and p75 antibodies, the staining by trkA antiserum was absent. While trkB antiserum labeled both the somata and processes of VGNs in the vestibular ganglion, trka antiserum failed to detect the presence of trkA protein in these neurons. When the cross sections of vestibular ganglion were double-labeled with a monoclonal antibody (N52) against neurofilament protein (200 Kd) which stains all processes and cell bodies of the VGNs, all neurofilament-positive VGNs were also immunoreactive to antiserum against trkB, but not to antiserum against trkA. In addition, a majority of VGNs were double labeled by an antiserum against p75, the low-affinity receptor for all neurotrophins. These results indicate that VGNs produce trkB and p75 proteins, but not trkA protein.

Example IV

NT-4/5, BDNF and NT-3 Protect VGNs Against Neurotoxicity of Ototoxic Drugs

The ability of trkB or trkC agonists to protect neurons from ototoxicity was determined using VGNs in cell culture. When cisplatin or gentamicin was added to the culture, a dose-dependent inhibition of VGN survival was observed (FIGS. 4 and 5). At a dose of 4 $\mu$g/ml of cisplatin or 3 mgiml of gentamicin, a majority of VGNs died in the culture. All human recombinant neurotrophins (Genentech, Inc.) were added to the cultures at the time of plating. To block the effects of the neurotrophins, 1 $\mu$g/ml of trkB-IgG or trkC-IgG (kindly provided by Dr. Dave Shelton), specific antagonists for NT-4/5 (and BDNF) or NT-3, respectively (Shelton et al., 1995), was added to some of the experimental cultures at the same time when neurotrophins were added. In some experiments, cisplatin (Bristol-Myers Squibb) or gentamicin sulfate (Sigma) was added at various concentrations at the time of plating, either alone or in combination with 10 ng/ml of different neurotrophins. In other experiments, epidermal growth factor (EGF), basic fibroblast growth factor ($\beta$FGF) and insulin-like growth factor-1 (IGF-1) were added to the culture at the time of plating at a concentration of 10 ng/ml. Cell counts and data analysis were performed as described in the above Examples except that in some cultures in which high concentrations of cisplatin or gentamicin were added, cell counts were made from the entire area of the culture wells because the overall number of viable VGNs was small. In these experiments, cell counts were performed in the same way for control cultures.

To examine whether neurotrophins could protect the VGNs from cisplatin neurotoxicity, neurotrophins were added together with 3 different doses of cisplatin. At 1 $\mu$g/ml or 2$\mu$g/ml of cisplatin, the number of surviving VGNs in the culture containing NT-4/5 was not only higher than that in the culture with cisplatin alone, but also higher than the control culture without cisplatin, indicating that NT-4/5 prevents the VGN from cisplatin neurotoxicity and promotes VGN survival. At 4 $\mu$g/ml of cisplatin, NT-4/5 still significantly ameliorated the toxic effects of cisplatin ($p<0.001$) and protected VGNs from cell death, although it was about 60% of the survival levels of control cultures in the absence of cisplatin (FIG. 4). An equivalent effectiveness of BDNF was observed against cisplatin neurotoxicity. Significant protective, but less potent effects were seen for NT-3. In contrast, NGF exhibited no protective effects (FIG. 4). Similar protective effects of NT-4/5, BDNF and NT-3 on VGNs were observed against neurotoxicity of gentamicin. As seen in the experiments with cisplatin, while NGF showed no effect, BDNF displayed an effect equivalent to NT-4/5, and NT-3 also exhibited significantly protective effect (FIG. 5). Finally, no additive effects were observed when NNT-4/55 was combined with BDNF or NT-3 in the culture containing cisplatin or gentamicin (FIG. 4 and FIG. 5).

Example V

Utricle Explant Cultures

An organotype utricle explant culture that utilizes a 3-D collagen matrix cultures and maintains its normal, in vivo architecture was prepared to provide a vestibular system. The utricle was dissected, with the vestibular ganglion attached, from P3 Wistar rats and cultured in three-dimensional ("3-D") collagen gel in serum free medium. In one embodiment a droplet (20 $\mu$m) of freshly made collagen gel which was placed on the bottom of a 35 mm Nunc tissue culture dish, modified from what described previously (Gao et al., 1991) as follows. Rat tail collagen (type I, Collaborative Research) was mixed with 10×BME medium and 2% sodium carbonate in a ratio of 10:1:1 and placed on ice just before use. The collagen matrix containing the utricle explant was incubated at 37° C. for 5–10 min until gellation. The matrix was then cultured in defined serum-free medium using sufficient medium to cover the explant (2 ml of serum-free medium (BME plus serum-free supplement (Sigma I-1884), 1% BSA, 2 mM glutamine, and 5 mg/ml glucose; containing no antibiotics) The culture medium was changed every other day thereafter.

Embedding the utricle explants in the 3-D collagen was better for maintaining their normal architecture than floating the explants or placing the explants on a monolayer substrate, since the explant tissue could be kept unfolded and cell migration out of the tissue could be limited. By using neurofilament (N52) and phalloidin-FITC conjugate double labeling, the integrity of VGNs and the hair cells in the utricle was demonstrated. Utricle explants prepared according to the invention maintained normal architecture in the 3-D collagen gel cultures as observed by Nomarski micrographs of utricle tissue dissected from P3 rats and grown for 2 days in vitro at low and high magnifications. The VGNs and hair cells in the explants grew well and maintained their normal connectivity. The VGNs and hair cells remained in their normal locations. No gross cell death of VGNs and hair cells occurred under this culture condition.

Example VI

Ototoxicity in Utricle Explant Cultures and Protective Effects of Neurotrophins in Utricle Explant Cultures Organotypic cultures of postnatal utricle explants provided herein, in which the innervation of hair cells by vestibular neurons are intact, are useful to examine ototoxicity of different classes of ototoxins, including ototoxic pharmaceutical drugs, for example, salicylate, gentamicin, and cisplatin, and to search for or test candidate agents that protect against the ototoxic effect. To determine if an ototoxin is able to induce degeneration of VGNs and/or hair cells in the utricle explant cultures, the ototoxin was added at different concentrations to the culture after allowing the culture to recover from the in vitro explant. Recovery typically occurred after two days. Histochemical double-labeling of the utricle explant cultures with a neurofilament antibody (e.g., Texas red-mediated; N52) and phalloidin (e.g., FITC-conjugated) were used to compare control cultures (untreated) with cultures treated with the ototoxin. While the neurofilament antibody (Texas red-mediated) labeled the VGNs, the phalloidin-FITC conjugate stained the hair cells. Typically three cultures per experimental paradigm were studied in each individual experiment. Three or more separate repetitions of the experiment were conducted to validate the ototoxic effect. Cell count of remaining hair cells and VGNs were performed. Since the density of the axons of VGNs appeared to be a reliable index of the number of surviving VGNs, the number of the VGN axons from a given length (100 $\mu$m) in the middle of the utricle was counted for different experimental groups and plotted. Phalloidin-labeled hair cells were also counted in the same way. In some of the experiments, improved accuracy was obtained by using serial cryostat sections (10 micrometer in thickness) for VGNs. Every fifth section was collected on one slide and stained with cresyl violet. Total number of remaining VGNs was determined as five-times the number of VGNs counted on the slide.

Neurotrophins are members of the NGF family of proteins. They have been widely shown to regulate the differentiation and survival of developing neurons (Korsching, 1993, Gao et al., 1995a) as well as to aid in the repairing or recovery of adult CNS neurons from injury and toxins (Hefti, 1986; Knusel et al., 1992; Yan et al, 1992; Gao et al., 1995b). They exert their biological functions through activation of high-affinity binding receptors, the trks with high characteristic specificity (Barbacid, 1993; Snider, 1994). As reported herein, VGNs express specific trk proteins. Hair cells express certain neurotrophin genes (Pirvola et al., 1992; Schecterson and Bothwell, 1994; Wheeler et al., 1994). In dissociated cell culture systems, as shown herein, specific neurotrophins promote survival of VGNs. As demonstrated herein neurotrophins protect VGNs from cisplatin ototoxicity. Similarly, as demonstrated for the first time herein, these neurotrophins also protect vestibular ganglion neurons from gentamicin in vitro. Of the four neurotrophins tested, NGF is ineffective. NT-4/5 and BDNF are equivalently and potently effective, and NT-3 displays a less potent but significant survival-promoting effect. The TrkB and TrkA immunohistochemistry on the sections of vestibular ganglia correlates strongly with the differential survival-promoting effects of NT-4/5, BDNF and NGF in VGN cultures. While the absence of immunostaining of TrkA antiserum is in agreement with the negative results of NGF on these neurons, the presence of TrkB protein in the VGNs in the present experiment suggests a direct action of NT-4/5 and BDNF on the VGNs. Consistent with these results, other growth factors including EGF, bFGF and IGF-1 show no detectable effects. The fact that addition of TrkB-IgG and TrkC-IgG to the culture specifically blocks the effects of NT-4/5, BDNF and NT-3 in the present study provides additional support for the notion of direct action of the three neurotrophins on VGNs. Given that the survival potency of NT-3 is lower than that of NT-4/5 and BDNF, it is quite possible that while most VGNs express TrkB gene, only a subset of these neurons co-express TrkC gene. The substantial loss of VGNs that has been reported for the TrkB knockout mice but not for the mice lacking the TrkC gene (Fritzsch et al., 1995) supports this notion.

Gentamicin, an aminoglycoside commonly used for treating diseases caused by Gram-negative bacteria, has unfortunate side effects of ototoxicity on both peripheral auditory and vestibular systems (Sera et al., 1987; Hinojosa and Lerner, 1987; Bareggi et al., 1990). Although it is generally believed that gentamicin destroys hair cells in all inner ear structures (Warchol et al., 1993; Lefebvre et al., 1993; Duckert and Rubel 1994), damage in the eighth nerve and cochleovestibular ganglion has also been observed (Sera et al., 1987; Hinojosa and Lerner, 1987). In the present experiments, gentamicin induced VGN cell death was observed at concentrations of 1–3 mg/ml, which appears to be somewhat higher than the concentrations (0.5–1 mg/ml) needed to destroy hair cells (Warchol et al., 1993; Lefebvre et al., 1993). Aminoglycosides at high concentration may directly damage VGNs in vivo (Hinojosa and Lerner, 1987).

It is interesting to note that VGNs are derived during neurogenesis from the same neurogenic placode as the primary auditory neurons in the spiral ganglia Both auditory neurons and VGNs send peripheral projections to hair cells of the inner ear and extend central projections to the brain stem. Spiral ganglion neurons are also protected from ototoxins by neurotrophins. While the central target seems to have little effect on the survival of the two neuronal types, the peripheral target promotes their survival (Ard et al., 1985). Neurotrophins protect VGNs from deleterious effects of cisplatin, but in addition, protect VGNs from gentamicin neurotoxicity. Although both types of neurons show similar responses to the neurotrophins and produce the same types of receptors for neurotrophins, there are noticeable differences in terms of efficacy of the three neurotrophins, which may reflect the ratio and level of neurotrophins available in the peripheral target and expression pattern of neurotrophin receptors in the two types of neurons. For example, NT-4/5 and BDNF promote the survival of spiral ganglion neurons up to 3-fold whereas only a 2-fold increase in the number of surviving VGNs is seen. In BDNF knockout mice, a majority of VGNs are lost, while primary auditory innervation remains unaffected (Ernfors et al., 1994). Similarly, when the NT-3 gene is deleted, the destruction of neurons in spiral ganglia is much more severe than in the vestibular ganglia (Farinas et al., 1994).

The results presented with organotypic cochlear explants are consistent with the dissociated neuronal culture findings. As the organotypic culture keeps the pertinent innervation of hair cells intact, it better represents the in vivo system and, consequently, allows exploration of the mechanism of actions of ototoxins and, most importantly, provides a system to discover and test candidate protective agents.

References

Anniko M, Sobin A (1986) Cisplatin: Evaluation of its ototoxic potential. Am J Otolaryngol 7:276–293.

Apfel S C, Lipton R B, Arezzo J C, Kessler J A (1991) Nerve growth factor prevents toxic neuropathy in mice. Ann. Neurol. 29:87–89.

Ard, M. D., Morest, D. K., and Hauger, S. H. (1985). Trophic interactions between the cochleovestibular ganglion of the chick embryo and its synaptic targets in culture. *Neurosci.* 16:151–170.

Au S, Weiner N D, Schacht J (1987) Aminoglycoside antibiotics preferentially increase permeability in phosphoinositide-containing membranes: a study with carboxyflurorescein in liposomes. Biochem. Biophys Acta 902:80–86.

Baired D H, Hatten M E, Mason C A (1992) Cerebellar target neurons provide a stop signal for affrent neurite extension in vitro. J. Neurosic. 12:619–634.

Barbacid, M. (1993). The trk family of neurotrophin receptors: molecular characterization and oncogenic activation in hauman tumors. *In Molecular Genetics of Nervous System Tumors.* Levin, A. G. and Schmidek, H. H., eds. (New York: Wiley-Liss), pp123–136.

Barde Y A, Edgar D, Thoenen H (1982) Purification of a new neurotrophic factor from mammalian brain. EMBO J. 1:549–553.

Bareggi, R., Grill, V., Narducci, P., Zweyer, M., Tesei, L, and Russolo, M. (1990). Genetamicin ototoxicity: Histological and ulstructural alterations after transtympanic administration. *Pharmacol. Res.* 22:635–644.

Barker, P. A., and Shooter, E. M. (1994). Disruption of NGF binding to the low affinity neurotrophin receptor $p_{75}^{LNTR}$ reduces NGF binding to trkA on PC12 cells. *Neuron* 13:203–215.

Berggren, D, Anniko, M, Thornell, L. -E., Ramaekers, F. C. S., and Virtanem, I. (1990). Intermediate filament proteins in the embryonic inner ear of mice under normal conditions and after exposure to ototoxic drugs. *Acta Otolaryngol.* (Stockh) 109:57–65.

Berkemeier L R, Winslow J W, Kaplan D R, Nikolics K, Goeddel D V, Rosenthal A (1991) Neurotrophin-5: A novel neurotrophic factor that activates trk and trkB. Neuron 7:857–866.

Boettcher F A, Bancroft B R, Salvi R J, Henderson D (1989) Effects of sodium salicylate on evoked-response measures of hearing. Hear Res 42: 129–142.

Boettcher F A, Bancroft B R, Salvi R J, Henderson D (1990) Concentration of salicylate in serum and perilymph of the chinchillla. Arch Otolaryngol Head Neck Surg 116:681–684.

Boettcher F A, Salvi R J (1991) Salicylate ototoxicity: review and synthesis. Am. J Otolaryngol 12: 33–47.

Carenza, L., Villani, C., Framarino dei Malatesta, M. L., Prosperi Porta, R., Millefiorine, M., Antonini, G., Bolasco, P., Bandiera, G., and Marzetti, L. (1986). Peripheral neuropathy and ototoxicity of dichlorodiamineplatinum: instrumental evaluation. *Gynecol. Oncol.* 25:244–249.

Chao, M. V., Bothwell, M. A., Ross, A. H., Koprowski, H., Lanahan, A. A., Buck, C. R., and Sehgal, A. (1986). Gene transfer and molecular cloning of the human NGF receptor. *Science* 232:518–521.

Chao, M. V. (1992). Growth factor signalling: where is the specificity? *Cell* 68:995–997.

Clary, D. O., and Reichardt, L. F. (1994). An alternatively spliced form of the nerve growth factor receptor trkA confers an enhanced response to neurotrophin 3. *Proc. Natl. Acad. Sci. USA* 91:11133–11137.

Clary, D. O., Weskamp, G., Austin, L. R., and Reichardt, L. F. (1994). trkA cross-linking mimics neuronal responses to nerve growth factor. *Mol. Biol. Cell* 5:549–563.

Cohen A, Bray G M, Aguayo A J (1994) Neurotrophin-4/5 (NT-4/5) increases adult rat retinal ganglion cell survival and neurite outgrowth in vitro. J. Neurobiol. 25:953–959.

Cordon-Cardo, C., Tapley, P., Jing, S., Nanduri, V., O'Rourke, E., Lamballe, F., Kovary, K., Klein, R., Jones, K. R., Reichhardt, L. F. and Barbacid, M. (1991), Cell, 66, 173–183

Corwin J T, Warchol M E (1991) Auditory hair cells: structure, function, development, and degeneration. Ann Rev Neurosci 14: 301–333.

Cotanche D A, Lee K H (1994) Regeneration of hair cells in the vestibulocochlear system of birds and mammals. Curr Opinion Neurobiol 4: 509–514.

Davies, A. M., Lee, K. F., and Jaenisch, R. (1993). p75-deficient trigeminal sensory neurons have an altered response to NGF but not to other neurotrophins. *Neuron* 11:565–574.

Davies A M, Horton A, Burton L E, Schmelzer C, Vandlen R, Rosenthal A (1993b) Neurotrophin-4/5 is a mammalian-specific survival factor for distinct populations of sensory neurons. J. Neurosci. 13:4961–4967.

Davies, A. M., Thoenen, H., and Barde, Y. -A. (1986). Different factors from the central nervous system and peripheral regulate the survival of sensory neurons. *Nature* 319:497–502.

De Moura L F P, Hayden R C (1968) Salicylate ototoxicity. Arch Otolaryng 87:60–64.

Dublin W B (1976) Fundamentals of sensorineural auditory pathology. Springfield, Ill.: C. C. Thomas.

Duckert, L. G., and Rubel, E. W. (1994). Morphological correlates of the functional recovery in the chicken inner ear after gentamicin treatment. *J. Comp. Neurol.* 331:75–96.

Ernfors P, Ibanez CF, Ebendal T, Olson L, Persson H (1990) Molecular cloning and neurotrophic activities of a protein with structural similarities to nerve growth factor: developmental and topographic expression in the brain. Proc. Natl. Acad. Sci. USA 87:5454–5458.

Ernfors, P., Lee, K. -F., and Jaenisch, R. (1994). Mice lacking brain-derived neurotrophic factor develop with sensory deficits. *Nature* 368:147–150.

Ernfors P, Loring J, Jaenisch R, Van De Water T R (1995) Function of neurotrophins in the auditory and vestibular systems: Analysis of BDNF and NT-3 gene knockout mice. Assoc. Res Otolaryngol Abstr p190.

Escandon E, Soppet D, Rosenthal A, Mendoza-Ramierz J-L, Szonyi E, Burton L E, Henderson C E, Parada L F, Nikolics K (1994) Regulation of neurotrophin receptor expression during embryonic and postnatal development. J. Neurosci. 14:2954–2068.

Falbe-Hansen J (1941) Clinical and experimental histological studies on effects of salicylate and quinine on the ear. Acta Otolaryng suppl 44: 1–216.

Farinas, I., Jones, K. R., Backus, C., Wang, X. -Y., and Reichardt, L. F. (1994). Severe sensory and sympathetic deficits in mice lacking neurotrophins-3. *Nature* 369:658–661.

Fischer W, Sirevaag A, Wiegand S J, Lindsay R M, Bj örklund A (1994) Reversal of spatial memory impairments in aged rats by nerve growth factor and neurotrophins 3 and 4/5 but not by brain-derived neurotrophic factor. Proc. Natl. Acad. Sci. USA 91:8607–8611.

Fleischman, R. W., Stadnicki, S. W., Ethier, M. F., and Schaeppi, U. (1975). Ototoxicity of cis-dichlorodiammine platinum (II) in the guinea pig. *Toxicol Appl. Pharmacol.* 33:320–332.

Forge A, Li L, Corwin J T, Nevill G (1993) Ultrastructural evidence for hair cell regeneration in the mammalian inner ear. Science 259:1616–1619.

Fritzsch, B., Smyene, R., Fagan, A., Selos-Santiago, I. (1995). Mice homologous for a non-functional trk-B receptor lack selectively in the innervation of semicircular canals. *Assoc. Res. Otolaryngol. Abstr.* p190.

Furley A, Morton SB, Malano D, Karagogeos, Dodd J, Jessell TM (1990) The axonal glycoprotein TAG-1 is an immunoglobin superfamily member with neurite outgrowth-promoting activity. Cell 61:157–170.

Gao W-Q, Heitz N, Hatten ME (1991) Cerebellar granule cell neurogenesis is regulated by cell-cell interactions in uitro. Neuron 6:705–715.

Gao W-Q, Dybdal N, Shinsky N, Murnane A, Schmelzer C, Siegel M, Keller G, Hefti F, Phillips HS, Winslow J W (1995b) Neurotrophin-3 reverses experimetal cisplatin-induced peripheral sensory neuropathy. Ann Neurol (1995) 38:30–37.

Gao, W. -Q., Zheng, J. L., and Karihaloo, M. (1995). Neurotrophin-4/5 (NT-4/5) and brain-derived neurotrophic factor (BDNF) act at later stages of cerebellar granule cell differentiation. *J. Neurosci.* 15:2656–2667.

Garner A S, Large T H (1994) Isoforms of the avian trkC receptor: A novel kinase insertion dissociates transformation and process outgrowth from survival. Neuron 13:457–472.

Gotz, R., Koster, R., Winkler, C., Raulf, F., Lottspelch, F., Scharti, M., and Thoenen, H. (1994). Neurotrophin-6 is a new member of the nerve growth factor family. *Nature* 372:266–269.

Grotz et al., Eur. J. Biochem. 204:745–749 (1992)

Guild S, Cowe S, Bunch C, Polvogt (1931) Correlations of differences in sensory of innervation of the organ of Corti with differences in the acuity of hearing, including evidences as to the location in the human cochlea of receptors for certain tones. Acta Otolaryngol. (Stockh) 15:269–308.

Hefti F (1986) Nerve growth factor (NGF) promotes survival of septal cholinergic neurons after fimbrial transections. J Neurosci 6:2155–2162.

Hinojosa, R., and Lerner, S. A. (1987). Cochlear neural degeration without hair cell loss in two patients with aminoglycoside ototoxicity. *J. Infect. Dis.* 156: 449–455.

Hohn A, Leibrock J, Bailey K, Barde Y A (1990) Identification and characterization of a novel member of the nerve growth factor/brain-derived neurotrophic factor family. Nature 344:339–341.

Hood J L, Berlin C I, Ed., *Contemporary applications of neurobiology in human hearing assessment* (Raven Press, New York, 1986).

Hulme, E. C. and Birdsall, M. J. M., Strategy and Tactics in Receptor Binding Studies, p63–212 in Receptor-Ligand Interactions, Ed. E. C. Hulme.

Hyman C, Hofer M, Barde Y A, Juhasz M, Yancopoulos G D, Squinto S P, Lindsay R M (1991) BDNF is a neurotrophic factor for dopaminergic neurons of the substantia nigra. Nature 350:230–233.

Hynes M A, Poulsen K, Armanini M, Berkemeier L, Phillips H, Rosenthal A (1994) Neurotrophin-4/5 is a survival factor for embryonic midbrain dopaminergic neurons in enriched cultures. J. Neurosci. Res. 37:144–154.

Ip N Y, Stitt T N, Tapley P, Klein R, Glass D J, Fandl J, Greene L A, Barbacid M, Yancopoulos G D (1993) Similarities and differences in the way neurotrophins interact with the trk receptors in neuronal and nonneuronal cells. Neuron 110:137–149.

Ip N Y, lbanez C F, Nye S H, McClain J, Jones P F, Gies D R, Belluscio L, LeBeau M M, Espinso III R, Squinto S P, Persson H, Yancopoulos G D (1992) Mammalian neurotrophin-4: Structure, chromosomal localization, tissue distribution, and receptor specificity. Proc. Nat. Acad. Sci. USA 89:3060–3064.

Jarvis J F (1966) A case of unilateral permanent deafness following acetyl salicylic acid. J Laryngol 80: 318–320.

Jones K R, Reichardt L F (1990) Molecular cloning of a human gene that is a member of the nerve growth factor family. Proc. Natl. Acad. Sci. USA 87:8060–8064.

Kaplan, D. R., Hempstead, B., Martin-Zanca, D., Chao, M., and Parada, L. F. (1991) Science 252, 554–558

Kaplan D R, Martin Z D, Parada L F (1991) Tyrosine phosphorylation and tyrosine kinase activity of the trk proto-oncogene product induced by NGF. Nature 350:158–160.

Kelley M W, Telreja D R, Corwin J T (1995) Replacement of hair cells after microbeam irradiation in cultured organs of Corti from embryonic and neonatal mice. J Neurosci 15:3013–3026.

Kelley M W, Xu X-M, Wagner M A, Warchol M E, Corwin J T (1993) The developing organ of Corti contains retinoic acid and forms supernumerary hair cells in response to exogenous retinoic acid in culture. Development 119:1041–1053.

Klein R, Jing S Q, Nanduri V, O'Rourke E, Barbacid M (1991a) The trk proto-oncogene encodes a receptor for nerve growth factor. Cell 65:189–197.

Klein R, Nanduri V, Jing S A, Lamballe F, Tapley P, Bryant S, Cordon-Cardo C, Jones K R, Reichardt L F, Barbacid M (1991b) The trkB tyrosine protein kinase is a receptor for brain-derived neurotrophic factor and neurotrophin-3. Cell 66:395–403.

Klein R, Martin-Zanca D, Barbacid M, Parada L F (1990) Expression of the tyrosine kinase receptor gene trkB is confined to the murine embryonic and adult nervous system. Development 109:845–850.

Klein, R., Lamballe, F., Bryant, S., and Barbacid, M. (1992) Neuron 8, 947–956

Klein, R., Parada, L. F., Coulier, F. and Barbacid, M. (1989), EMBO J., 8, 3701–3709.

Knusel B, Beck K D, Winslow J W, Rosenthal A, Burton L E, Widmer H R, Nikolics K, Hefti F (1992) Brain-derived neurotrophic factor administration protects basal forebrain cholinergic but not nigral dopaminergic neurons from degenerative changes after axotomy in the adult rat brain. J Neurosci 12:4391–4402.

Koliatsos V E, Clatterbuck R E, Winslow J W, Cayouette M H, Price D L (1993) Evidence that brain-derived neurotrophic factor is a trophic factor for motor neurons in vivo. Neuron 10:359–367.

Konings P N M, Makkink W K, van Delft A M L, Ruigt G S F (1994) Reversal by NGF of cytostatic drug-induced reduction of neurite outgrowth in rat dorsal root ganglia in vitro. Brain Res 640:195–204.

Kopf-Maier P, Muhlhausen S K (1992) Changes in the cytoskeleton pattern of tumor cells by cisplatin in vitro. Chem. Biol Interact 82:295–316.

Korsching, S. (1993). The neurotrophic factor concept: A reexamination. *J. Neurosci.* 13:2739–2748.

Lamballe F, Klein R, Barbacid M (1991) trkC, a new member of the trk family of tyrosine protein kinase, is a receptor for neurotrophin-3. Cell 66:967–979.

Lambert P R (1994) Inner ear hair cell regeneration in a mammal: identification of a triggering factor. Laryngoscope 104:701–718.

Lärkfors L, Ebendal T, Lindsay R M, Alderson R F (1993) Effects of neurotrophins on rat embryonic cerebellar purkinje cells in vitro. Abstr. Soc. Neurosci. 19:A278.14.

Leake P A, Snyder R L, Hradek G T, Rebscher S J (1992) Chronic intracochlear electrical stimulation in neonatally deafened cats: effects of intensity and stimulating electrod location. Hear Res 64:99–117.

Lefebvre P P, Malgrange B, Staecher H, Moghadass M, Van De Water T R, Moonen G (1994) Neurotrophins affect survival and neuritogenesis by adult injured auditory neurons in vitro. NeuroReport 5:865–868.

Lefebvre, P. P., Malgrange, B., Staecker, H., Moonen, G. and Van De Water, T. R. (1993). Retinoic acid stimulates regeneration of mammalian auditory hair cells. *Science* 260:692–695.

Lefebvre, P. P., Van De Water, T. R., Represa, J., Liu, W., Bernd, P., Modlin, S., Moonen, G., and Mayer, M. B.

(1991). Temporal pattern of nerve growth factor (NGF) binding in vivo and the in vitro effects of NGF on cultures of developing auditory and vestibular neurons. *Acta Otolaryngol* (Stockh) 111:304–311.

Lefebvre P P, Malgrange B, Moonen G, Van De Water T R (1995) Response to: Regeneration and mammalian auditory hair cells. Science 267: 709–711.

Leibrock J, Lottspeich F, Hohn A, Hofer M, Hengerer B, Masiakowski P, Thoenen H, Barde Y A (1989) Molecular cloning and expression of brain-derived neurotrophic factor. Nature 341:149–152.

Levi-Montalcini R (1987) The nerve growth factor: thirty-five years later. EMBO J. 6:1145–1154.

Lim D J (1986) Effects of noise and ototoxic drugs at the cellular level in the cochlea: A review. Am J Otolaryngol 7: 73–99.

Lippe W R, Hathaway O, Parlotz D (1995) Loss of avian spiral ganglion neurons following aminoglycosie-induced hair cell loss and regeneration. Assoc Res Otolaryngol Abstr. p84.

Maisonpierre P C, Belluscio L, Squinto S, Ip N Y, Furth M E, Lindsay R M, Yancopoulos G D (1990) Neurotrophin-3: a neurotrophic factor related to NGF and BDNF. Science 247:1446–1451.

Martin-Zanca, D., Oskam, R., Mitra, G., Copeland, T. and Barbacid, M. (1989), Mol. Cell. Biol., 9, 24–33.

McAlpine D, Johnstone B M (1990) The ototoxic mechanism of cisplatin. Hear Res 47:191–204.

McCabe P, Dey F (1965) The effects of aspirin upon auditory sensitivity. Ann Otol 74: 312–324.

Mollman J E (1990) Cisplatin neurotoxicity. N. Engl. J. Med. 322:126–127.

Myers E N, Berstaein J M (1965) Salicylate ototoxicity: A clinical and experimental study. Arch Otolaryngl Head Neck Surg 82: 483–493.

Nakai, Y., Konishi, K., Chang, K. C., Ohashi, K., Morisaki, N., Minowa, Y., and Morimoto, A. (1982). Ototoxicity of the anticancer drug cisplatin. *Acta Otolaryngol* 93:227–232.

Pirvola, U., Yikoski, J., Palgi, J., Lehtonen, E., Arumäe, U., and Saarma, M. (1992). Brain-derived neurotrophic factor and neurotrophin 3 mRNAs in the peripheral target fields of developing inner ear ganglia. Proc. Natl. Acad. Sci. USA 89:9915–9919.

Pryor G (1994) Assessment of auditory dysfunction. In Principle of Neurotoxicology. Chang L W, ed., Marcel Dekker, Inc. PP345–371.

Rastel D, Abdouh A, Dahl D, Roman R (1993) An original organotypic culture method to study the organ of Corti of the newborn rat in vitro. J Neurosci Methods 47:123–131.

Richardson G P, Russell I J (1991) Cochlear cultures as a model system for studying aminoglycoside ototoxicity. Hear Res 53:293–311.

Roelofs, R. I., Hrushesky, W., Rogin, J., and Rosenberg, L. (1984). Peripheral sensory neuropathy and cisplatin chemotherapy. *Neurology* 34:934–938.

Rosenthal A, Goeddel D, Nguyen T, Lewis M, Shih A, Laramee G R, Nikolics K, Winslow J W (1990) Primary structure and biological activity of a novel human neurotrophic factor. Neuron 4:767–773.

Rybak L P (1986) Ototoxic mechanisms. In: Neurobiology of Hearing. Altschuler R A, Bobbin R P, Hoffman DW, Eds. Raven Press (New York) PP441–454.

Schacht J (1986) Molecular mechanisms of drug-induced hearing loss. Hear Res 22: 297–304.

Schecterson, L. C., and Bothwell, M. (1994). Neurotrophin and neurotrophin receptor mRNA expression in developing inner ear. *Hear. Res.* 73:92–100.

Scopes, R., Protein Purification, Springer-Verlag, NY (1982).

Sera, K., Harada, Y., Tagashira, N., Suzuki, M., Hirakawa, K., and Ohya, T. (1987). Morphological changes in the vestibular epithelia and ganglion induced by ototoxic drug. *Scanning Microsc.* 1:1191–1197.

Shelton, D. L., Sutherland, J., Gripp, J., Camertato, T., Armanini, M. P., Phillips, H. S., Carroll, K., Spencer, S. D., and Levinson, A. D. (1995). Human trks: Molecular cloning, tissue distribution, and expression of extracellular domain immunoadhesins. *J. Neurosci.* 15:477–491.

Siegal T, Haim N (1990) Cisplatin-induced peripheral neuropathy. Cancer 66:1117–1123.

Snider, W, D, (1994), Functions of the neurotrophins during nervous system development: What the knockouts are teaching us. *Cell* 77: 627–638.

Sobkowicz H M, Bereman B, Rose J E (1975) Organotypic development of the organ of Corti in culture. J. neurocytol. 4:543–572.

Soppet D, Escandon E, Maragos J, Middlemas D S, Reid S W, Blair J, Burton L E, Stanton B R, Kaplan D R, Hunter T, Nikolics K, Parada L F (1991) The neurotrophic factors brain-derived neurotrophic factor and neurotrophin-3 are ligands for the trkB tyrosine kinase receptor. Cell 65:895–903.

Squinto S P, Stitt T N, Aldrich T H, Davis S, Bianco S M, Radziejewski C, Glass D J, Masiakowski P, Furth M E, Valenzuela D M, DiStefano P S, Yancopoulos G D (1991) trkB encodes a functional receptor for brain-derived neurotrophic factor and neurotrophin-3 but not nerve growth factor. Cell 65:885–893.

Stadnicki, S. W., Fleischman, R. W., Schaeppi, U., and Merriam, P. (1975). Cis-dichlorodiammineplatinum (II) (NSC-119875): Hearing loss and other toxic effects in rhesus monkeys. *Cancer Chemother. Rep.* 59:467–480.

Thompson, S. W., Davis, L. E., Kornfeld, M., Hilgers, R. D., and Standefer, J. C. (1984). Cisplatin neuropathy. *Cancer* 54:1269–1275.

Tsoulfas P, Soppet D, Escandon E, Tessarollo L, Mendoza-Ramirez J-L, Rosenthal A, Nikolics K, Parada L F (1993) The rat trkC locus encodes multiple neurogenic receptors that exhibit differential response to neurotrophin-3 in PC12 cells. Neuron 10:975–990.

Tsue T T, Oesterle E C, Rubel E W (1994a) Diffusible factors regulate hair cell regeneration in the avian inner ear. Proc Natl Acad. Sci USA 91:1584–1588.

Tsue T T, Oesterle E C, Rubel E W (1994b) Hair cell regeneration in the inner ear. Otolaryngol. Head Neck Surg 111:281–301.

Valenzuela D M, Maisonpierre P C, Glass D J, Rojas E, Nunez L, Kong Y, Gies D R, Stitt T N, Ip N Y, Yancopoulos G D (1993) Alternative forms of rat trkC with different functional capabilities. Neuron 10: 963–974.

Vazquez E, Van De Water T R, Del Valle M, Veta J A, Staecker H, Giráldez F, Represa J (1994) Pattern of trkB protein-like immunoreactivity in vivo and the in vitro effects of brain-derived neurotrophic factor (BDNF) on developing cochlear and vestibular neurons. Anat. Embryol. 189:157–167.

Verdi, J. M., Birren, S. J., Ibanez, C. F., Persson, H., Kaplan, D. R., Benedett, M., Chao, M. V., and Anderson, D. J. (1994). $p75^{LNGFR}$ regulates trk signal transduction and NGF-induced neuronal differentiation in MAH cells. *Neuron* 12:733–745.

Von Bartheld, C. S., Patterson, S. L., Heuer, J. G., Wheeler, E. F., Bothwell, M., and Rubel, E. W. (1991). Expression of nerve growth factor (NGF) receptors in the developing inner ear of chick and rat. *Development* 113: 455–470.

Warchol, M. E., Lambert, P. R., Goldstein, B. J., Forge, A., and Corwin, J. T. (1993). Regenerative proliferation in inner ear sensory epithelia from adult Guinea pigs and humans. *Science* 259:1619–1622.

Weskamp, G., and Reichardt, L. F. (1991). Evidence that biological activity of NGF is mediated through a novel subclass of high affinity receptors. *Neuron* 6:649–663.

Wheeler, E. F., Bothwell, M, Schecterson, L. C., and Von Bartheld, C. S. (1994). Expression of BDNF and NT-3 mRNA in hair cells of the organ of corti: Quantitative analysis in developing rats. *Hear. Res.* 73:46–56.

Windebank A J, Smith A G, Russell J W (1994) The effect of nerve growth factor, ciliary neurotrophic factor, and ACTH analogs on cisplatin neurotoxicity in vitro. Neurology 44: 488–494.

Wittmaack K (1903) Beitrage zur Kenntnis der Wirkung des Chinins auf das Gehoerorgan. Pflueger Arch Ges Physiol 95:237.

Woodford C M, Henderson D, Hamernik R P (1978) Effects of combinations of sodium salicylate and noise on the auditory threshold. Ann Otol Rhinol Laryngol 87:117–127.

Yamashita H, Oesterle E C (1995) Induction of cell proliferation in mammalian inner-ear sensory epithelia by transforing growth factor a and epidermal growth factor. Proc Natl Acad Sci USA 92:3152–3155.

Yan Q, Elliott J L, Snider W D (1992) Brain-derived neurotrophic factor rescues spinal motoneurons from axotomy induced cell death. Nature 360:753–755.

Yan, Q., Matheson, C., Sun, J., Radeke, M. J., Feinstein, S. C., and Miller, J. A. (1994). Distribution of intracerebral ventricularly administered neurotrophins in rat brain and its correlation with trk receptor expression. *Exper. Neurology* 127:23–36.

Ylikoski, J., Pirvola, U., Moshnyakov, M., Palgi, J., Arumae, U., and Saarma, M. (1993). Expression patterns of neurotrophin and their receptor mRNAs in the rat inner ear. *Hear. Res.* 65:69–78.

---

What is claimed is:

1. A pharmaceutical composition, comprising a pharmaceutical agent capable of ototoxin-induced balance impairment and a trkB or trkC agonist in an amount therapeutically effective for treating ototoxicity caused by the pharmaceutical agent, wherein said agonist is
    (a) a NT-4/5 (SEQ ID NO:1) variant comprising one to five amino acid alterations selected from the group consisting of: G78-->K, H, Q or R, R85-->E, F, P, Y or W, a conservative amino acid substitution at any of positions R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118, 65NAE67→NAS or NAT, ΔC78, ΔC61, ΔQ54–ΔT59, ΔR60–ΔD82, ΔH85–ΔS88, ΔW86–ΔT101, R53→H, K91→H, V108→F, R84→Q, H, N, T, Y or W, D116→E, N, Q, Y, S, or T, wherein Δ indicates deletion of a single amino acid or deletion of the indicated span of residues, inclusive; or
    (b) a NT-4/5 (SEQ ID NO:1) fragment selected from the group consisting of NT-4/5(R83–Q94), NT-4/5 (G1–C61), NT-4/5(G1–C17), NT-4/5(C17–C61), NT-4/5(C17–C78), NT-4/5(C17–C90), NT-4/5 (C17–C119), NT-4/5(C17–C121), NT-4/5(R11–R27), NT-4/5(R11–R34), NT-4/5(R34–R53), NT-4/5 (C61–C78), NT-4/5(R53–C61), NT-4/5(C61–C119), NT-4/5(C61–C78), NT-4/5(C78–C119), NT-4/5 (C61–C90), NT-4/5(R60–C78), NT-4/5(K62–C119), NT-4/5(K62–K91), NT-4/5(R79–R98), NT-4/5 (R83–R93), NT-4/5(T101–R111), NT-4/5(G1–C121) VLTVKRVRR (SEQ ID NO:4), NT-4/5(V40–C121) VLTVKRVRR (SEQ ID NO:5), NT-4/5(V40–C121) SLTIKRIRA (SEQ ID NO:6), NT-4/5(V40–C121) TLSRKAGRRA (SEQ ID NO:7), DDDSPIARRGEIS-VCDSVSDWVSAPDKDTAVDIKGDDVMV-LKKVGINHSV (SEQ ID NO:8), and NT-4/5 (V40–C121).

2. The pharmaceutical composition of claim 1, wherein the ototoxic pharmaceutical agent is selected from the group consisting of an aminoglycoside antibiotic and an antineoplastic agent.

3. The pharmaceutical composition of claim 1, further comprising a hair cell growth factor.

4. A method for treating neuronal-related balance impairment in a mammal, comprising administering to a mammal in need of such treatment a therapeutically effective amount of a trkB or trkC agonist wherein said agonist is
    (a) a NT-4/5 (SEQ ID NO:1) variant comprising one to five amino acid alterations selected from the group consisting of: G78→K, H, Q or R, R85→E, F, P, Y or W, a conservative amino acid substitution at any of positions R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118, 65NAE67→NAS or NAT, ΔC78, ΔC61, ΔQ54–ΔT59, ΔR60–ΔD82, ΔH85–ΔS88, ΔW86–ΔT101, R53→H, K91→H, V108→F, R84→Q, H, N, T, Y or W, D116→E, N, Q, Y, S, or T, wherein Δ indicates deletion of a single amino acid or deletion of the indicated span of residues, inclusive; or
    (b) a NT-4/5 (SEQ ID NO:1) fragment selected from the group consisting of NT-4/5(R83–Q94), NT-4/5 (G1–C61), NT-4/5(G1–C17), NT-4/5(C17–C61), NT-4/5(C17–C78), NT-4/5(C17–C90), NT-4/5 (C17–C119), NT-4/5(C17–C121), NT-4/5(R11–R27), NT-4/5(R11–R34), NT-4/5(R34–R53), NT-4/5 (C61–C78), NT-4/5(R53–C61), NT-4/5(C61–C119), NT-4/5(C61–C78), NT-4/5(C78–C119), NT-4/5 (C61–C90), NT-4/5(R60–C78), NT-4/5(K62–C119), NT-4/5(K62–K91), NT-4/5(R79–R98), NT-4/5 (R83–R93), NT-4/5(T101–R111), NT-4/5(G1–C121) VLTVKRVRR (SEQ ID NO:4), NT-4/5(V40–C121) VLTVKRVRR (SEQ ID NO:5), NT-4/5(V40–C121) SLTIKRIRA (SEQ ID NO:6), NT-4/5(V40–C121) TLSRKAGRRA (SEQ ID NO:7), DDDSPIARRGEIS-VCDSVSDWVSAPDKDTAVDIKGDDVMV-LKKVGINHSV (SEQ ID NO:8), and NT-4/5 (V40–C121).

5. The method of claim 4, wherein the balance impairment is ototoxin induced.

6. The method of claim 5, wherein the ototoxicity affects vestibular ganglion neurons.

7. The method of claim 6, wherein the ototoxicity results from administration of a therapeutically effective amount of an ototoxic compound selected from the group consisting of a chemotherapeutic agent and an antibiotic.

8. The method of claim 7, wherein the antibiotic is an aminoglycoside antibiotic.

9. The method of claim 8, wherein the aminoglycoside antibiotic is selected from the group consisting of neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin.

10. The method of claim 7, wherein the ototoxic compound is a chemotherapeutic agent.

11. The method of claim 10, wherein the ototoxic compound is cisplatin.

12. The method of claim 7, wherein the trkB or trkC agonist is administered prior to administration of an ototoxin.

13. The method of claim 4, wherein the trkB or trkC agonist is administered with an agent that promotes hair cell growth or regeneration.

14. The method of claim 4, which further comprises administering an effective amount of a second trkB or trkC agonist.

15. The method of claim 14, wherein the second agonist comprises a chimeric or pantropic neurotrophin.

16. The method of claim 15, wherein the pantropic neurotrophin is MNTS-1.

17. An improved method for treatment of infection of a mammal by administration of an aminoglycoside antibiotic, the improvement comprising administering a therapeutically effective amount of a trkB or trkC agonist to the mammal in need of such treatment to reduce ototoxin-induced balance impairment associated with the antibiotic, wherein said agonist is (a) a NT-4/5 (SEQ ID NO:1) variant comprising one to five amino acid alterations selected from the group consisting of: G78→K, H, Q or R, R85→E, F, P, Y or W, a conservative amino acid substitution at any of positions R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118, 65NAE67→NAS or NAT, ΔC78, ΔC61, ΔQ54–ΔT59, ΔR60–ΔD82, ΔH85–ΔS88, ΔW86–ΔT101, R53→H, K91→H, V108→F, R84→Q, H, N, T, Y or W, D116→E, N, Q, Y, S, or T, wherein Δ indicates deletion of a single amino acid or deletion of the indicated span of residues, inclusive; or (b) a NT-4/5 (SEQ ID NO:1) fragment selected from the group consisting of NT-4/5(R83–Q94), NT-4/5 (G1–C61), NT-4/5(G1–C17), NT-4/5(C17–C61), NT-4/5(C17–C78), NT-4/5(C17–C90), NT-4/5 (C17–C119), NT-4/5(C17–C121), NT-4/5(R11–R27), NT-4/5(R11–R34), NT-4/5(R34–R53), NT-4/5 (C61–C78), NT-4/5(R53–C61), NT-4/5(C61–C119), NT-4/5(C61–C78), NT-4/5(C78–C119), NT-4/5 (C61–C90), NT-4/5(R60–C78), NT-4/5(K62–C119), NT-4/5(K62–K91), NT-4/5(R79–R98), NT-4/5 (R83–R93), NT-4/5(T101–R111), NT-4/5(G1–C121) VLTVKRVRR (SEQ ID NO:4), NT-4/5(V40–C121) VLTVKRVRR (SEQ ID NO:5), NT-4/5(V40–C121) SLTIKRIRA (SEQ ID NO:6), NT-4/5(V40–C121) TLSRKAGRRA (SEQ ID NO:7), DDDSPIARRGEIS-VCDSVSDWVSAPDKDTAVDIKGDDVMV-LKKVGINHSV (SEQ ID NO:8), and NT-4/5 (V40–C121).

18. An improved method for the treatment of cancer in a mammal by administration of a chemotherapeutic compound, the improvement comprising administering a therapeutically effective amount of a trkB or trkC agonist to the mammal in need of such treatment to reduce ototoxin-induced balance impairment associated with the chemotherapeutic drug, wherein said agonist is (a) a NT-4/5 (SEQ ID NO:1) variant comprising one to five amino acid alterations selected from the group consisting of: G78→K, H, Q or R, R85→E, F, P, Y or W, a conservative amino acid substitution at any of positions R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118, 65NAE67→NAS or NAT, ΔC78, ΔC61, ΔQ54–ΔT59, ΔR60–ΔD82, ΔH85–ΔS88, ΔW86–ΔT101, R53→H, K91→H, V108→F, R84→Q, H, N, T, Y or W, D116→E, N, Q, Y, S, or T, wherein Δ indicates deletion of a single amino acid or deletion of the indicated span of residues, inclusive; or (b) a NT-4/5 (SEQ ID NO:1) fragment selected from the group consisting of NT-4/5(R83–Q94), NT-4/5 (G1–C61), NT-4/5(G1–C17), NT-4/5(C17–C61), NT-4/5(C17–C78), NT-4/5(C17–C90), NT-4/5 (C17–C119), NT-4/5(C17–C121), NT-4/5(R11–R27), NT-4/5(R11–R34), NT-4/5(R34–R53), NT-4/5 (C61–C78), NT-4/5(R53–C61), NT-4/5(C61–C119), NT-4/5(C61–C78), NT-4/5(C78–C119), NT-4/5 (C61–C90), NT-4/5(R60–C78), NT-4/5(K62–C119), NT-4/5(K62–K91), NT-4/5(R79–R98), NT-4/5 (R83–R93), NT-4/5(T101–R111), NT-4/5(G1–C121) VLTVKRVRR (SEQ ID NO:4), NT-4/5(V40–C121) VLTVKRVRR (SEQ ID NO:5), NT-4/5(V40–C121) SLTIKRIRA (SEQ ID NO:6), NT-4/5(V40–C121) TLSRKAGRRA (SEQ ID NO:7), DDDSPIARRGEIS-VCDSVSDWVSAPDKDTAVDIKGDDVMV-LKKVGINHSV (SEQ ID NO:8), and NT-4/5 (V40–C121).

19. A method for promoting vestibular ganglion neuron survival prior to, upon, or after exposure to an ototoxin or an injury causing neuronal damage, loss or degeneration, comprising administering to the neuron an effective amount of a trkB or trkC agonist, wherein said agonist is (a) a NT-4/5 (SEQ ID NO:1) variant comprising one to five amino acid alterations selected from the group consisting of: G78→K, H, Q or R, R85→E, F, P, Y or W, a conservative amino acid substitution at any of positions R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118, 65NAE67→NAS or NAT, ΔC78, ΔC61, ΔQ54–ΔT59, ΔR60–ΔD82, ΔH85–ΔS88, ΔW86–ΔT101, R53→H, K91→H, V108→F, R84→Q, H, N, T, Y or W, D116→E, N, Q, Y, S, or T, wherein Δ indicates deletion of a single amino acid or deletion of the indicated span of residues, inclusive; or (b) a NT-4/5 (SEQ ID NO:1) fragment selected from the group consisting of NT-4/5(R83–Q94), NT-4/5 (G1–C61), NT-4/5(G1–C17), NT-4/5(C17–C61), NT-4/5(C17–C78), NT-4/5(C17–C90), NT-4/5 (C17–C119), NT-4/5(C17–C121), NT-4/5(R11–R27), NT-4/5(R11–R34), NT-4/5(R34–R53), NT-4/5 (C61–C78), NT-4/5(R53–C61), NT-4/5(C61–C119), NT-4/5(C61–C78), NT-4/5(C78–C119), NT-4/5 (C61–C90), NT-4/5(R60–C78), NT-4/5(K62–C119), NT-4/5(K62–K91), NT-4/5(R79–R98), NT-4/5 (R83–R93), NT-4/5(T101–R111), NT-4/5(G1–C121) VLTVKRVRR (SEQ ID NO:4), NT-4/5(V40–C121) VLTVKRVRR (SEQ ID NO:5), NT-4/5(V40–C121) SLTIKRIRA (SEQ ID NO:6), NT-4/5(V40–C121) TLSRKAGRRA (SEQ ID NO:7), DDDSPIARRGEIS-VCDSVSDWVSAPDKDTAVDIKGDDVMV-LKKVGINHSV (SEQ ID NO:8), and NT-4/5 (V40–C121).

* * * * *

SEQUENCE LISTING

<160> NUMBER OF SEQ ID NOS: 37

<210> SEQ ID NO 1
<211> LENGTH: 130
<212> TYPE: PRT
<213> ORGANISM: Homo sapiens

<400> SEQUENCE: 1

```
Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala His Ala Gln
                95                  100                 105

Gly Arg Val Gly Trp Arg Trp Ile Arg Ile Asp Thr Ala Cys Val
                110                 115                 120

Cys Thr Leu Leu Ser Arg Thr Gly Arg Ala
                125                 130
```

<210> SEQ ID NO 2
<211> LENGTH: 119
<212> TYPE: PRT
<213> ORGANISM: Homo sapiens

<400> SEQUENCE: 2

```
Tyr Ala Glu His Lys Ser His Arg Gly Glu Tyr Ser Val Cys Asp
 1               5                  10                  15

Ser Glu Ser Leu Trp Val Thr Asp Lys Ser Ser Ala Ile Asp Ile
                20                  25                  30
```

-continued

```
Arg Gly His Gln Val Thr Val Leu Gly Glu Ile Lys Thr Gly Asn
                 35                  40                  45

Ser Pro Val Lys Gln Tyr Phe Tyr Glu Thr Arg Cys Lys Glu Ala
                 50                  55                  60

Arg Pro Val Lys Asn Gly Cys Arg Gly Ile Asp Asp Lys His Trp
                 65                  70                  75

Asn Ser Gln Cys Lys Thr Ser Gln Thr Tyr Val Arg Ala Leu Thr
                 80                  85                  90

Ser Glu Asn Asn Lys Leu Val Gly Trp Arg Trp Ile Arg Ile Asp
                 95                 100                 105

Thr Ser Cys Val Ser Ala Leu Ser Arg Lys Ile Gly Arg Thr
                110                 115
```

<210> SEQ ID NO 3
<211> LENGTH: 118
<212> TYPE: PRT
<213> ORGANISM: Homo sapiens

<400> SEQUENCE: 3

```
His Ser Asp Pro Ala Arg Arg Gly Glu Leu Ser Val Cys Asp Ser
  1               5                  10                  15

Ile Ser Glu Trp Val Thr Ala Ala Asp Lys Lys Thr Ala Val Asp
                 20                  25                  30

Met Ser Gly Gly Thr Val Thr Val Leu Glu Lys Val Pro Val Ser
                 35                  40                  45

Lys Gly Gln Leu Lys Gln Tyr Phe Tyr Glu Thr Lys Cys Asn Pro
                 50                  55                  60

Met Gly Tyr Thr Lys Glu Gly Cys Arg Gly Ile Asp Lys Arg His
                 65                  70                  75

Trp Asn Ser Gln Cys Arg Thr Thr Gln Ser Tyr Val Arg Ala Leu
                 80                  85                  90

Thr Met Asp Ser Lys Lys Arg Ile Gly Trp Arg Phe Ile Arg Ile
                 95                 100                 105

Asp Thr Ser Cys Val Thr Leu Thr Ile Lys Arg Gly Arg
                110                 115
```

<210> SEQ ID NO 4
<211> LENGTH: 9
<212> TYPE: PRT
<213> ORGANISM: Homo sapiens

<400> SEQUENCE: 4

```
Val Leu Thr Val Lys Arg Val Arg Arg
  1               5
```

<210> SEQ ID NO 5
<211> LENGTH: 9
<212> TYPE: PRT
<213> ORGANISM: Homo sapiens

<400> SEQUENCE: 5

```
Val Leu Thr Val Lys Arg Val Arg Arg
  1               5
```

<210> SEQ ID NO 6
<211> LENGTH: 9
<212> TYPE: PRT
<213> ORGANISM: Homo sapiens

<400> SEQUENCE: 6

-continued

Ser Leu Thr Ile Lys Arg Ile Arg Ala
1               5

<210> SEQ ID NO 7
<211> LENGTH: 10
<212> TYPE: PRT
<213> ORGANISM: Homo sapiens

<400> SEQUENCE: 7

Thr Leu Ser Arg Lys Ala Gly Arg Arg Ala
1               5                   10

<210> SEQ ID NO 8
<211> LENGTH: 50
<212> TYPE: PRT
<213> ORGANISM: Homo sapiens

<400> SEQUENCE: 8

Asp Asp Asp Ser Pro Ile Ala Arg Arg Gly Glu Ile Ser Val Cys
1               5                   10                  15

Asp Ser Val Ser Asp Trp Val Ser Ala Pro Asp Lys Asp Thr Ala
                20                  25                  30

Val Asp Ile Lys Gly Asp Asp Val Met Val Leu Lys Lys Val Gly
                35                  40                  45

Ile Asn His Ser Val
                50

<210> SEQ ID NO 9
<211> LENGTH: 4
<212> TYPE: PRT
<213> ORGANISM: Homo sapiens

<400> SEQUENCE: 9

Ile Lys Thr Gly
1

<210> SEQ ID NO 10
<211> LENGTH: 5
<212> TYPE: PRT
<213> ORGANISM: Homo sapiens

<400> SEQUENCE: 10

Glu Ile Lys Thr Gly
1               5

<210> SEQ ID NO 11
<211> LENGTH: 6
<212> TYPE: PRT
<213> ORGANISM: Homo sapiens

<400> SEQUENCE: 11

Glu Ile Lys Thr Gly Asn
1               5

<210> SEQ ID NO 12
<211> LENGTH: 4
<212> TYPE: PRT
<213> ORGANISM: Homo sapiens

<400> SEQUENCE: 12

Ser Pro Val Lys
1

```
<210> SEQ ID NO 13
<211> LENGTH: 4
<212> TYPE: PRT
<213> ORGANISM: Homo sapiens

<400> SEQUENCE: 13

Lys Ser Ser Ala
  1

<210> SEQ ID NO 14
<211> LENGTH: 6
<212> TYPE: PRT
<213> ORGANISM: Homo sapiens

<400> SEQUENCE: 14

Tyr Ala Glu His Lys Ser
  1               5

<210> SEQ ID NO 15
<211> LENGTH: 7
<212> TYPE: PRT
<213> ORGANISM: Homo sapiens

<400> SEQUENCE: 15

Arg Tyr Ala Glu His Lys Ser
  1               5

<210> SEQ ID NO 16
<211> LENGTH: 8
<212> TYPE: PRT
<213> ORGANISM: Homo sapiens

<400> SEQUENCE: 16

Arg Tyr Ala Glu His Lys Ser His
  1               5

<210> SEQ ID NO 17
<211> LENGTH: 7
<212> TYPE: PRT
<213> ORGANISM: Homo sapiens

<400> SEQUENCE: 17

Tyr Ala Glu His Lys Ser His
  1               5

<210> SEQ ID NO 18
<211> LENGTH: 5
<212> TYPE: PRT
<213> ORGANISM: Homo sapiens

<400> SEQUENCE: 18

Ala Asn Arg Thr Ser
  1               5

<210> SEQ ID NO 19
<211> LENGTH: 4
<212> TYPE: PRT
<213> ORGANISM: Homo sapiens

<400> SEQUENCE: 19

Ala Asn Arg Thr
  1

<210> SEQ ID NO 20
```

```
<211> LENGTH: 4
<212> TYPE: PRT
<213> ORGANISM: Homo sapiens

<400> SEQUENCE: 20

Asn Arg Thr Ser
 1

<210> SEQ ID NO 21
<211> LENGTH: 4
<212> TYPE: PRT
<213> ORGANISM: Homo sapiens

<400> SEQUENCE: 21

Lys Glu Ala Arg
 1

<210> SEQ ID NO 22
<211> LENGTH: 5
<212> TYPE: PRT
<213> ORGANISM: Homo sapiens

<400> SEQUENCE: 22

Lys Glu Ala Arg Pro
 1               5

<210> SEQ ID NO 23
<211> LENGTH: 4
<212> TYPE: PRT
<213> ORGANISM: Homo sapiens

<400> SEQUENCE: 23

Ile Asp Asp Lys
 1

<210> SEQ ID NO 24
<211> LENGTH: 4
<212> TYPE: PRT
<213> ORGANISM: Homo sapiens

<400> SEQUENCE: 24

Ser Glu Asn Asn
 1

<210> SEQ ID NO 25
<211> LENGTH: 5
<212> TYPE: PRT
<213> ORGANISM: Homo sapiens

<400> SEQUENCE: 25

Thr Ser Glu Asn Asn
 1               5

<210> SEQ ID NO 26
<211> LENGTH: 6
<212> TYPE: PRT
<213> ORGANISM: Homo sapiens

<400> SEQUENCE: 26

Thr Ser Glu Asn Asn Lys
 1               5

<210> SEQ ID NO 27
<211> LENGTH: 4
<212> TYPE: PRT
```

-continued

<213> ORGANISM: Homo sapiens

<400> SEQUENCE: 27

Lys Leu Val Gly
 1

<210> SEQ ID NO 28
<211> LENGTH: 5
<212> TYPE: PRT
<213> ORGANISM: Homo sapiens

<400> SEQUENCE: 28

Gly Gly Ser Gly Gly
 1               5

<210> SEQ ID NO 29
<211> LENGTH: 10
<212> TYPE: PRT
<213> ORGANISM: Homo sapiens

<400> SEQUENCE: 29

Gln Cys Arg Thr Thr Gln Ser Tyr Val Arg
 1               5                  10

<210> SEQ ID NO 30
<211> LENGTH: 6
<212> TYPE: PRT
<213> ORGANISM: Homo sapiens

<400> SEQUENCE: 30

Ser Lys Lys Arg Ile Gly
 1               5

<210> SEQ ID NO 31
<211> LENGTH: 120
<212> TYPE: PRT
<213> ORGANISM: Homo sapiens

<400> SEQUENCE: 31

Ser Ser Ser His Pro Ile Phe His Arg Gly Glu Phe Ser Val Cys
 1               5                  10                  15

Asp Ser Val Ser Val Trp Val Gly Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Thr Thr Thr His Thr Phe Val Lys Ala Leu
                80                  85                  90

Thr Met Asp Gly Lys Gln Ala Ala Trp Arg Phe Ile Arg Ile Asp
                95                 100                 105

Thr Ala Cys Val Cys Val Leu Ser Arg Lys Ala Val Arg Arg Ala
               110                 115                 120

<210> SEQ ID NO 32
<211> LENGTH: 120
<212> TYPE: PRT
<213> ORGANISM: Homo sapiens

<400> SEQUENCE: 32

```
Ser Ser Ser His Pro Ile Phe His Arg Gly Glu Tyr Ser Val Cys
  1               5                  10                  15

Asp Ser Glu Ser Leu Trp Val Thr Asp Lys Ser Ser Ala Ile Asp
                 20                  25                  30

Ile Arg Gly His Gln Val Thr Val Leu Gly Glu Ile Lys Thr Gly
                 35                  40                  45

Asn Ser Pro Val Lys Gln Tyr Phe Tyr Glu Thr Arg Cys Lys Glu
                 50                  55                  60

Ala Arg Pro Val Lys Asn Gly Cys Arg Gly Ile Asp Asp Lys His
                 65                  70                  75

Trp Asn Ser Gln Cys Lys Thr Ser Gln Thr Tyr Val Arg Ala Leu
                 80                  85                  90

Thr Ser Glu Asn Asn Lys Leu Val Gly Trp Arg Trp Ile Arg Ile
                 95                 100                 105

Asp Thr Ser Cys Val Ser Ala Leu Ser Arg Lys Ile Gly Arg Thr
                110                 115                 120

<210> SEQ ID NO 33
<211> LENGTH: 7
<212> TYPE: PRT
<213> ORGANISM: Homo sapiens

<400> SEQUENCE: 33

Tyr Ala Ser His Pro Ile Phe
  1               5

<210> SEQ ID NO 34
<211> LENGTH: 6
<212> TYPE: PRT
<213> ORGANISM: Homo sapiens

<400> SEQUENCE: 34

Tyr Ala His Pro Ile Phe
  1               5

<210> SEQ ID NO 35
<211> LENGTH: 7
<212> TYPE: PRT
<213> ORGANISM: Homo sapiens

<400> SEQUENCE: 35

Tyr Ala Ser His Pro Ile Ser
  1               5

<210> SEQ ID NO 36
<211> LENGTH: 7
<212> TYPE: PRT
<213> ORGANISM: Homo sapiens

<400> SEQUENCE: 36

Tyr Ala Glu His Pro Ile Phe
  1               5

<210> SEQ ID NO 37
<211> LENGTH: 7
<212> TYPE: PRT
<213> ORGANISM: Homo sapiens
```

<400> SEQUENCE: 37

Tyr Ala Gln His Pro Ile Phe
1               5